(12) United States Patent
Ishikawa et al.

(10) Patent No.: US 6,295,466 B1
(45) Date of Patent: Sep. 25, 2001

(54) WIRELESS EKG

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/478,320

(22) Filed: Jan. 6, 2000

Related U.S. Application Data

(60) Provisional application No. 60/115,193, filed on Jan. 6, 1999.

(51) Int. Cl.[7] .................................................. A61B 5/0402
(52) U.S. Cl. .......................................... 600/509; 600/377
(58) Field of Search ..................................... 600/373, 374, 600/377, 509

(56) References Cited

U.S. PATENT DOCUMENTS 5,564,429   10/1996   Bornn et al. ..................... 128/696

FOREIGN PATENT DOCUMENTS

| 0 617 914 A1 | 10/1994 | (EP) | ............................. A61B/5/0402 |
| 0 738 496 A1 | 10/1996 | (EP) | ................................. A61B/5/00 |
| 0 209 804 | 1/1997 | (EP) | ................................. A61B/5/07 |
| WO 94/01039 | 1/1994 | (WO) | ................................. A61B/5/04 |
| WO 98/25090 | 6/1998 | (WO) | ............................. F27B/15/00 |

*Primary Examiner*—Scott M. Getzow
(74) *Attorney, Agent, or Firm*—Howison, Chauza, Thoma, Handley & Arnott, L.L.P.

(57) ABSTRACT

A wireless electrocardiogram monitor utilizing a cooperative association of miniature semiconductor balls. A side view of a surface mount cardiac monitor system (200) shows three semiconductor electrode balls (202), (204), and (206) contacting a central communication ball (208) for electrical communication therebetween. Each of the electrode balls (202), (204), and (206) have fabricated thereon a respective electrode (210), (212), and (214) for receiving electrical signals from the heart. The electrode signals are passed to the central communication ball (208) for processing, filtering, digital conversion, and transmission therefrom to a remote control system being operated by a medical technician. The data can then be displayed to medical personnel.

42 Claims, 12 Drawing Sheets

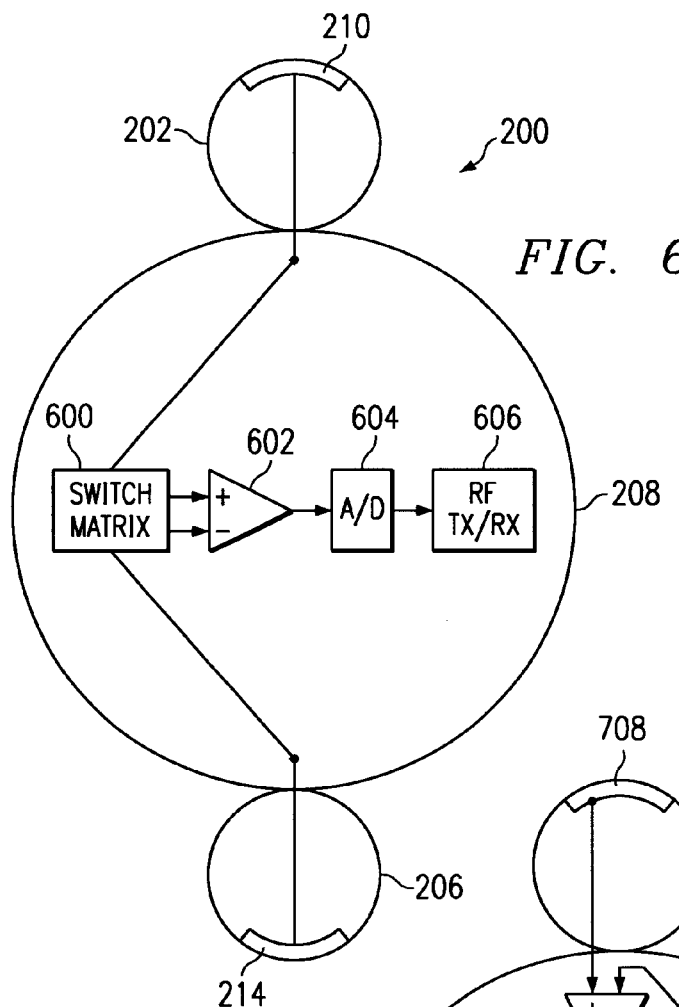
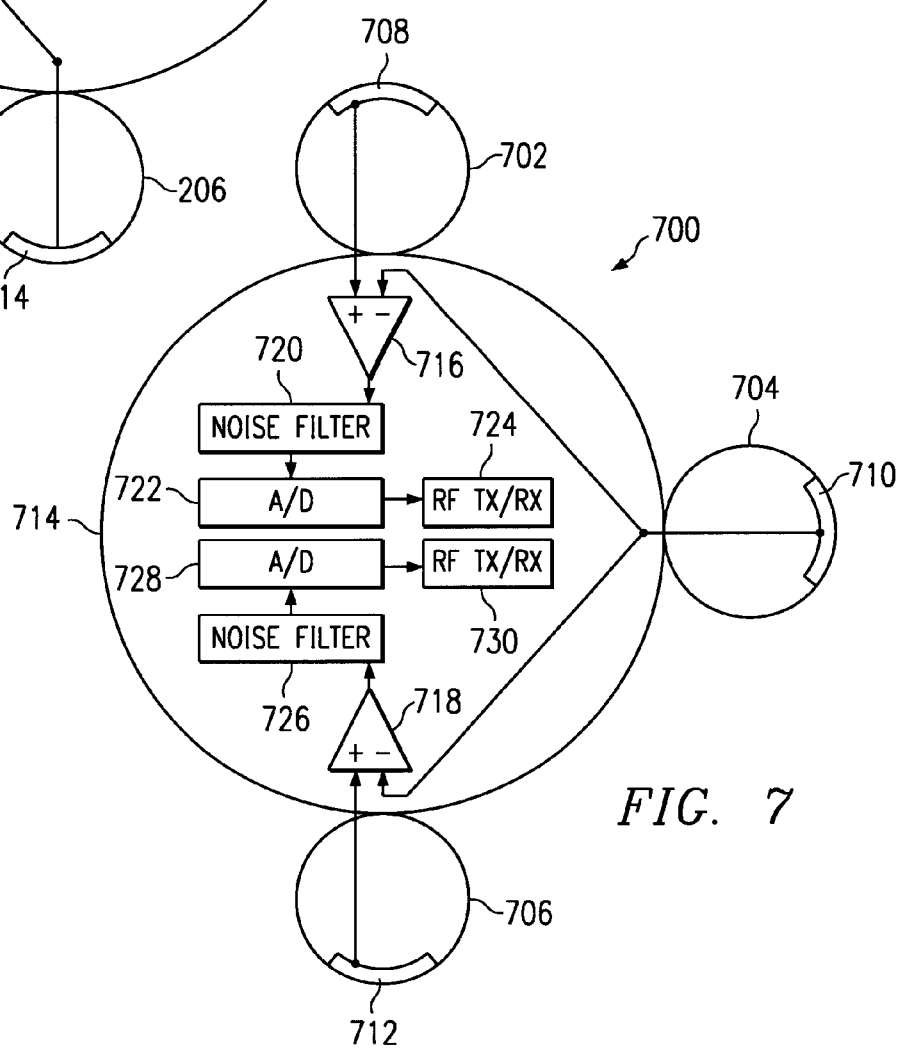

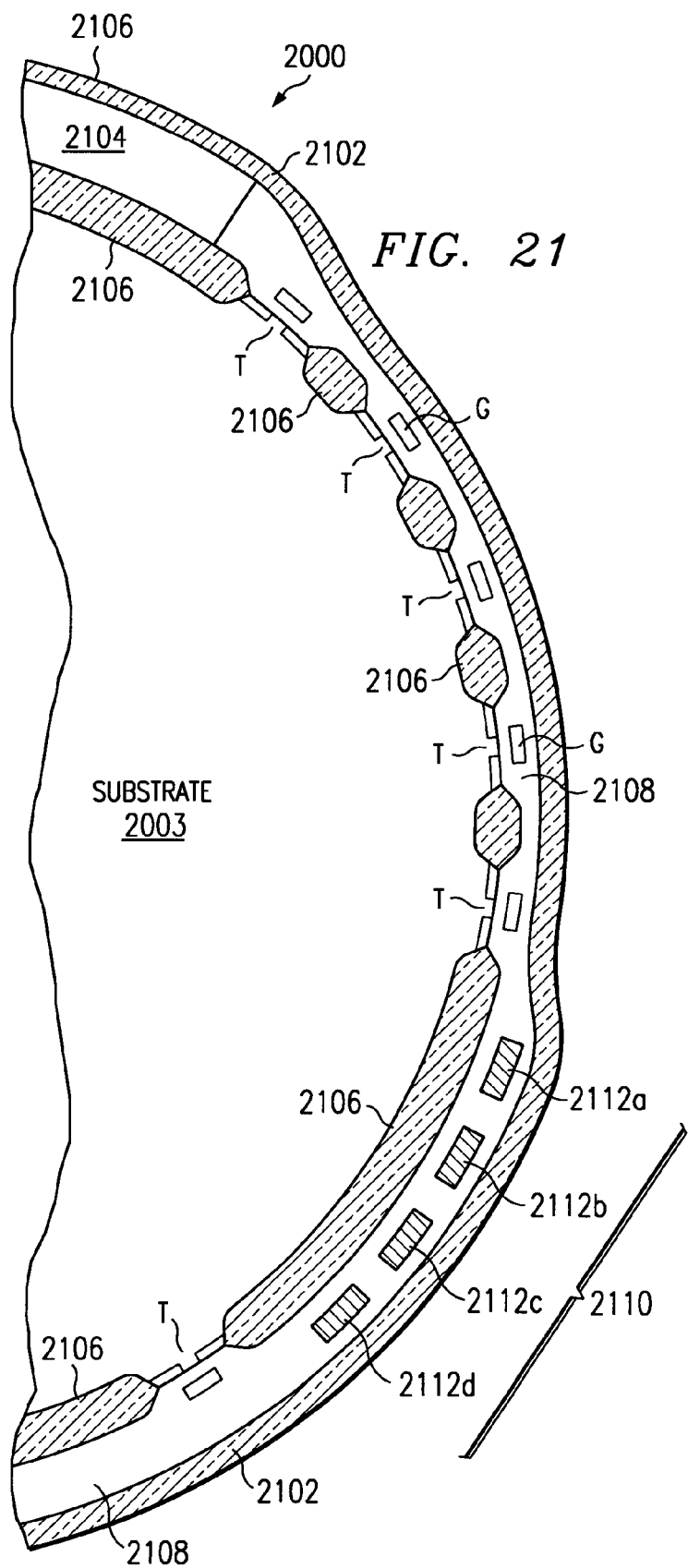

WIRELESS EKG

CROSS-REFERENCE TO RELATED APPLICATIONS

This application claims priority under 35 U.S.C. 119(e) from U.S. Provisional patent application Ser. No. 60/115,193 filed on Jan. 6, 1999, having the same title as this application.

This application is related to co-pending U.S. patent application Ser. No. 09/321,862 entitled "X-RAY IMAGING APPARATUS USING SPHERICAL SEMICONDUCTOR DETECTORS," filed May 28, 1999; U.S. patent application Ser. No. 09/323,585 entitled "IMPLANTABLE EPICARDIAL ELECTRODE," filed Jun. 2, 1999; U.S. Provisional patent application Ser. No. 60/137,100 entitled "METHOD AND APPARATUS FOR ATTACHING TAGS TO MEDICAL DEVICES," filed Jun. 2, 1999; U.S. patent application Ser. No. 09/448,641 entitled "INTRALUMINAL MONITORING SYSTEM," filed Nov. 24, 1999; U.S. patent application Ser. No. 09/448,781 entitled "SPHERICALLY-SHAPED BIOMEDICAL IC," filed Nov. 24, 1999; U.S. patent application Ser. No. 09/448,642 entitled "MINIATURE SPHERICAL-SHAPED SEMICONDUCTOR WITH TRANSDUCER," filed Nov. 24, 1999; and U.S. Provisional patent application Ser. No. 06/163,656 entitled "MEDICALLY IMPLANTED ACCELEROMETER," filed Nov. 3, 1999, each of which is herein incorporated by reference.

TECHNICAL FIELD OF THE INVENTION

This invention is related to a cutaneous medical sensing device and more particularly to a miniature ball-shaped electrode sensing device with wireless communication capabilities.

BACKGROUND OF THE INVENTION

The cardiac cycle can be described as the activation of certain specialized heart conduction cells in a predictable sequence which leads to a coordinated and sequential contraction of the atrial and ventricular muscle fibers. This sequence of events, culminating in a cardiac contraction, leads to effective circulation of blood to vital parts of the body. Normally, heart activation is an ordered sequence of electrical depolarization and repolarization from the sinoatrial node to the ventricular fibers. Effective cardiac contraction is thus dependent upon the anatomical distribution and electrical properties of these specialized fibers. Voltage variations are generated from the depolarization and repolarization of the specialized cardiac fibers which creates electrical fields that reach the body surface. A surface electrocardiogram is a graph of these voltage variations plotted over time.

Cardiac monitoring is a critical component of all emergency rooms, critical care units, and telemetry beds. Abnormalities of cardiac rhythm may be the first sign of an impending cardiopulmonary arrest and can be prevented with early detection and treatment. The monitors in current use utilize surface electrodes located on the body connected by wires to an electrocardiographic machine which allows the detected heart signal to be displayed on a paper strip or a monitor screen. Alternatively, these wires can be connected to a small but cumbersome relay box hung around the patient's neck. Often these relay boxes or monitors cannot be used during critical tests such as with imaging studies using magnetic resonance.

The normal electrocardiogram is obtained from one of three types of electrical connections. These connections are known as limb leads, augmented limb leads, and precordial leads. Limb leads are bipolar leads in which two electrodes are used to detect electrical variations at two points and the difference between these signals is what is displayed. Augmented limb leads are unipolar in that one electrode is used to detect electrical variations in potential at one site on the body and then compared to an electrode located at a site where electrical activity does not vary much with the cardiac cycle. For instance, one electrode could be connected to either a right arm, left arm, or leg and the generated signal can be compared to a signal from an electrode located at a point which does not vary significantly in electrical activity during cardiac contraction. The precordial leads are also unipolar, but unlike the augmented limb leads, one or more precordial electrodes are connected to the chest wall. The generated signal(s) is compared to a signal generated by an electrode located at a point which again does not vary significantly with the cardiac cycle. The current state of the art requires wire connections between these surface electrodes to generate the resultant electrocardiogram.

In an ideal lead system for monitoring electrical activity of the heart, the electrodes should be perpendicular to each other, the amplitude detected by each electrode should be roughly equal, and each electrode should have the same signal strength and direction for all points in the heart where electrical forces are generated. These ideal electrodes have been termed corrected "orthogonal leads." Orthogonal lead systems have recently been constructed on implantable subcutaneous cardiac monitors for detecting and recording episodes of cardiac syncope. A disadvantage of these implantable monitors is the need for surgical placement and the limited usefulness for short term cardiac monitoring situations which occur in emergency or operating rooms and in the critical care facility or elsewhere.

SUMMARY OF THE INVENTION

The present invention disclosed and claimed herein, in one aspect thereof, comprises a surface cardiac monitor system for monitoring electrical activity of the heart. The system comprises one or more semiconductor electrode balls having respective electrode sensors for sensing electrical heart activity, a central processing semiconductor ball having each of the one or more semiconductor electrode balls connected electrically thereto for receiving respective heart signals from the sensors of the electrode balls, and processing the heart signals for transmission via wireless communication; and a remote control system for receiving the transmitted heart signals and extracting heart information from the transmitted heart signal about the electrical activity of the heart.

BRIEF DESCRIPTION OF THE DRAWINGS

For a more complete understanding of the present invention and the advantages thereof, reference is now made to the following description taken in conjunction with the accompanying Drawings in which:

FIG. 6 illustrates an enlargement of a central semiconductor ball having a schematic representation of the circuitry required for processing electrical signals received from each of the electrodes;

FIG. 7 illustrates a 4-ball surface monitor having signals which are processed in a parallel non-linear fashion;

FIG. 21 illustrates additional semiconductor details of a semiconductor processor ball;

DETAILED DESCRIPTION OF THE INVENTION

The disclosed architecture provides a surface mount cardiac monitor system and the circuitry required for selectively detecting and comparing electrical signals received by any combination of electrode (cathode-anode) pairs present on the surface cardiac monitor used in the system and the processing, integration, conversion, and transmission of said signals to an offsite central processing unit for storage or viewing.

Figure 1:
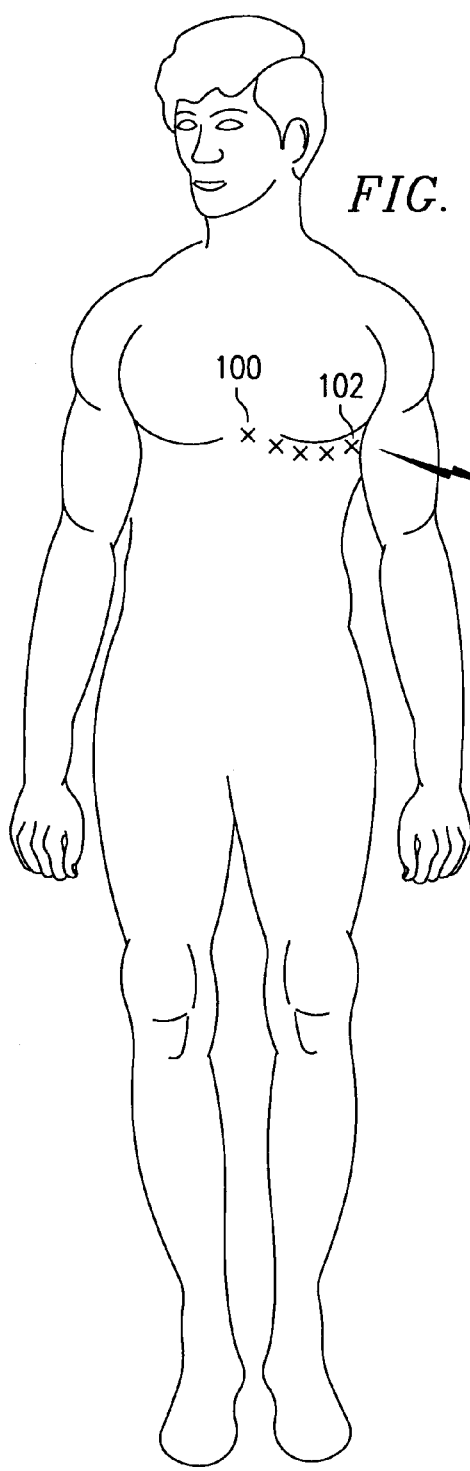
FIG. 1 illustrates a frontal view of a human body having a torso marked with one or more locations for the placement of the disclosed ball semiconductor surface mount EKG monitors.

Referring now to FIG. 1, there is illustrated a frontal view of a human body having a torso marked with one or more locations for the placement of the disclosed ball semiconductor surface mount EKG monitors. In this particular embodiment, the monitor(s) may be placed over the precordium anywhere from the sternum 100 to the anterior axillary line in the $5^{th}$ intercostal space 102. There is provided a control center 104 for wirelessly interfacing with the monitor(s), as will be described in greater detail hereinbelow.

Figure 2B:
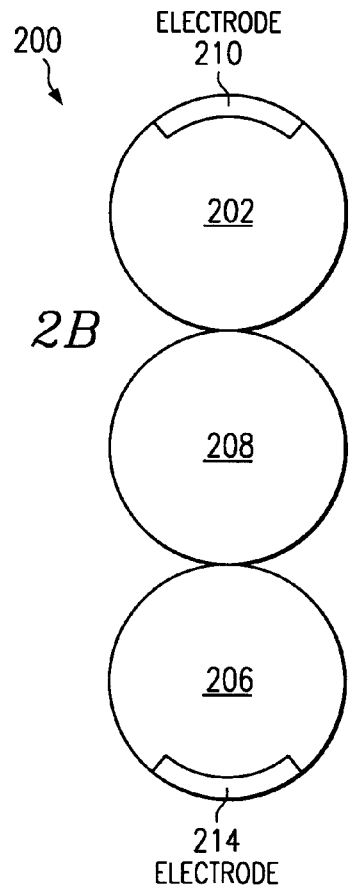
FIGS. 2A and 2B illustrate side and front views of a surface mount cardiac monitor utilizing four semiconductor ball ICs, according to a disclosed embodiment.
Figure 2A:
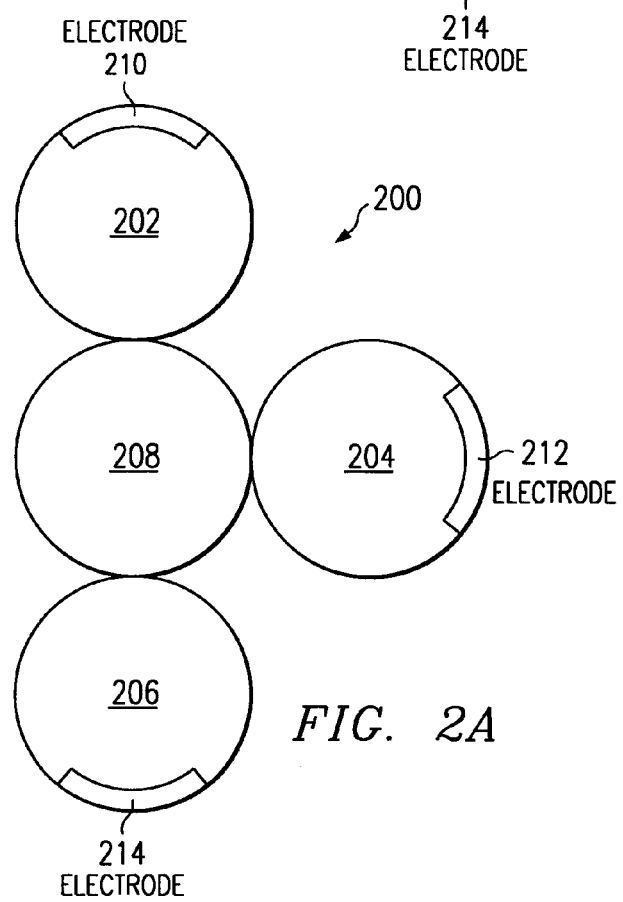

Referring now to FIGS. 2A and 2B, there are illustrated side and front views of a surface mount cardiac monitor 200 utilizing four semiconductor ball ICs, according to a disclosed embodiment. In FIG. 2A, a side view of the surface cardiac monitor system 200 shows three semiconductor electrode ball ICs 202, 204, and 206 contacting a central communication ball 208 for electrical communication therebetween. Each of the electrode balls 202, 204, and 206 have fabricated thereon a respective electrode 210, 212, and 214 for receiving electrical signals from the heart. These electrodes would be arranged in an orthogonal relationship to each other as displayed in FIG. 2A. The frontal view of FIG. 2B further illustrates the orthogonal relationship of the electrode balls 202 and 206 to the central communication ball 208. This redundant orthogonal arrangement is intended to obtain an electrocardiogram not only with information concerning the rhythm of the heart, but also to supply information with regards to cardiac ischemia, injury, or presence of necrosis. As these electrodes are in close proximity, they will be electrically isolated from each other by a suitable insulating material. A more detailed discussion of the contact interconnections between the balls is discussed hereinbelow.

Figure 3:
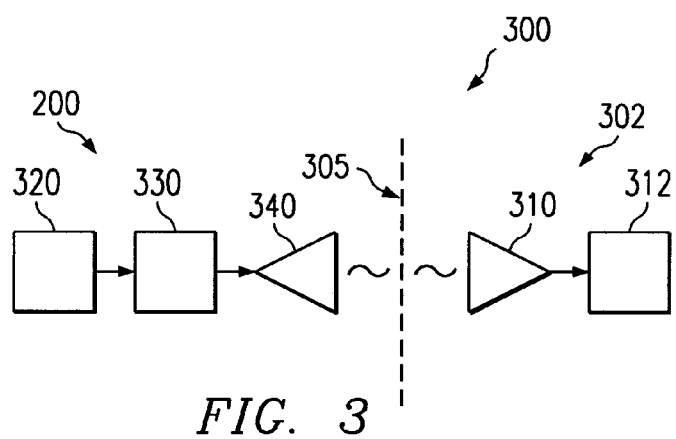
FIG. 3 illustrates a general system block diagram of a remote control system and the monitor.

Referring now to FIG. 3, there is illustrated a general system block diagram of a remote control system and the monitor 200. A surface cardiac monitor system 300 is illustrated for monitoring electrical activity of the heart, and comprises a remote control system 302 for interacting with and receiving data from the monitor system 200 attached to the skin of the human body, the dashed line 305 indicating the human body having the monitor system 200 attached thereon and the control system 302 located remoter thereto. (Note that where necessary, the disclosed monitor system 200 may also be inserted under the skin to obtain the same results.) The monitor system 200 contains a detector 320 for detecting the electrical activity of the heart from three orthogonal points and generating a signal indicative of the detected electrical heart activity; a processor 330 for processing the generated electrical signal for transmission from the surface cardiac monitor 200 using wireless communication; a transmitter 340 for wirelessly transmitting the generated electrical signal to the remote location 302; a receiver/transmitter 310 at the remote location 302 for receiving the electrical signal; and a processor 312 at the remote location 302 for processing the received electrical signal for the purpose of extracting therefrom the information about the detected electrical activity of the heart.

Figure 4:
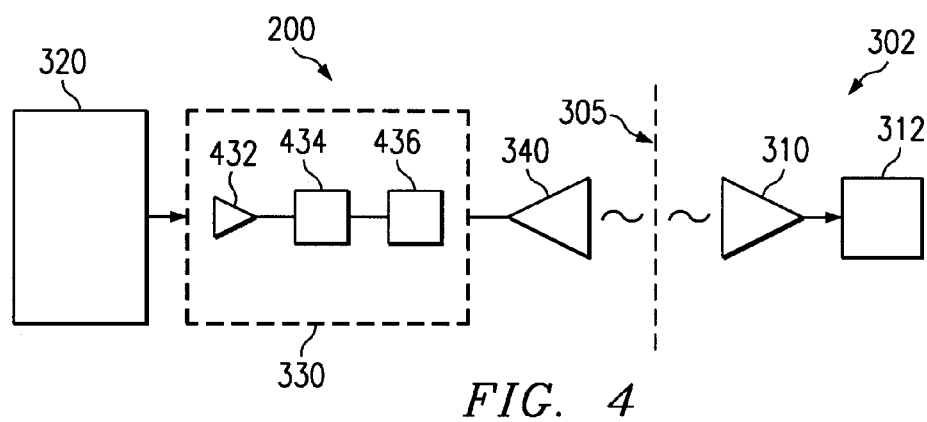
FIG. 4 illustrates a more detailed block diagram of the monitor processor for processing the sensed cardiac electrical signal.

Referring now to FIG. 4, there is illustrated a more detailed block diagram of the monitor processor 330 for processing the sensed cardiac electrical signal. The processor 330 comprises a comparator amplifier 432, a noise filter 434, and an analog-to-digital (A/D) converter 436. The comparator amplifier 432 receives the electrical signals generated by each of the three electrodes 210, 212, 214, and generates an analog signal indicative of the comparison of the signals of one of the three electrode pairs (210/212, 210/214, or 212/214). The noise filter 434 removes noise signals generated by and picked up from skeletal muscle contractions, and the A/D converter 436 converts the analog signal into a digital representative of the detected electrical heart activity for transmission to the remote location 302 using wireless communication. Preferably, the wireless transmission mechanism (which comprises transmitter/receiver devices 340 and 310) for transmitting the digitized electrical signal is a telemetry transmitter device operating at radio frequency (RF). Any wireless transmission technique may be used. In addition, the remote location 302 receives the digitized transmitted electrical signal using a compatible RF telemetry receiver device or some other wireless receiver that is compatible with the transmitted signal.

Figure 5:
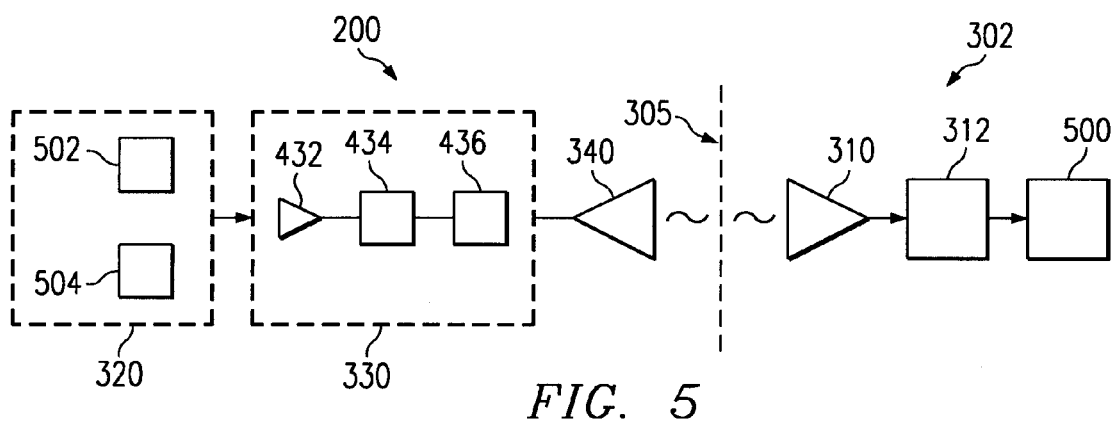
FIG. 5 illustrates the surface cardiac monitor system further comprising a display for displaying the interpreted digitized electrical signal.

Referring now to FIG. 5, there is illustrated the surface cardiac monitor system 200 further comprising a display 500 for displaying the interpreted digitized electrical signal. On the monitor system 200, the detector 320 is illustrated having two electrodes 502 and 504 which can detect electrical activity of the heart. The output of the electrodes 502 and 504 is input to the processor 330 for conditioning of the detected heart signal prior to transmission by the transmitter/receiver unit 340 from the monitor system 200 to the remoter control station 302. The measured electrical signal can then be presented to the technician via the display 500.

As seen from the foregoing drawings, the surface monitor 200 thus contains the capability of comparing and processing electrical signals from any of the three orthogonal electrodes (210, 212, and 214) of the monitor 200 by a series of switching circuits and signal processors. These signals are then amplified and filtered, and converted from an analog to a digital signal using the processor 330. The digital signal is then wirelessly transmitted to the remote location 302 via RF transmission techniques for further processing.

Referring now to FIG. 6, there is illustrated an enlargement of a central semiconductor ball having a schematic representation of the circuitry required for processing electrical signals received from each of the electrodes 210, 212, and 214. Pairs of electrode signals can be compared using switching circuitry which allows these signals to be separately processed through parallel linear and nonlinear combinational processing circuitry and separately transmitted to the remote location 302 for off-site comparison. Signals detected from electrodes 210, 212, and 214 (only 210 and 214 are shown coupled in this frontal view) to a central switching device (or matrix) 600 which allows an electrocardiogram signal to be developed across pairs of electrodes (210/212 and 212/214). The switching matrix 600 is operable to input selected pairs of electrode outputs into a comparator 602 (similar to comparator/amplifier 432) under control of the onboard processor (not shown) of the monitor system 200. For example, in a first mode, the switching matrix 600 passes the outputs of electrodes 210 and 214 into the comparator 602. In a second mode, the outputs of electrodes 210 and 212 are passed into the comparator 602, and a third mode selects the outputs of electrodes 212 and 214 to be fed into the comparator 600. This signal is then amplified and routed to an analog/digital converter 604 to derive a signal for RF transmission using a transmit/receive circuit 606 to a central processing unit (CPU) (not shown) external to the monitor 200.

The surface cardiac monitor 200 would generate a signal of a specific radio frequency which is transmitted to the CPU. Within the CPU, signals are compared from each surface cardiac monitor 200 and the maximal signal is selected for conversion back to an analog signal (electrocardiogram) for display on the viewing device 500, or for storage. In a busy emergency room where multiple patients are to be monitored, specific identification tags will be tied to each RF signal to allow for proper orientation of each signal, i.e., radio frequency signals from bed X will be received and processed only by the CPU for bed X, and not the CPU for bed Y. In this way, two or more signals taken from the surface cardiac monitors 200 would be always available to the remote location processor 312. Thus, if one of the signals were weaker due to the orientation of the monitor 200, the other electrodes which are not so oriented would not be so influenced and could provide a continuous generated signal on the heart activity irrespective of monitor orientation.

Referring now to FIG. 7, there is illustrated a 4-ball surface monitor 700 (similar to monitor 200) having signals which are processed in a parallel non-linear fashion. The central processor ball 714 has been enlarged to include the block diagram when in practice, the central processor ball 714 is substantially the same size as the electrode balls 702, 704, and 706. Each of three electrode balls 702, 704, and 706 have respective electrodes 708, 710, and 712. Signals from each of the electrodes 708, 710, and 712 passed from the electrode balls 702, 704, and 706 to a central processing ball 714, where they are amplified and filtered prior to digital conversion and transmission to a remote CPU (not shown). The disclosed embodiment shows two independent processing circuits, each having a comparator, a noise filter, and A/D, and a transmit/receive circuit.

In operation, the signal from electrode 710 is compared to both the signal of electrode 708 and the signal of electrode 712, resulting in two independent signal transmissions being sent from the central processing ball 714 to the remote control system 302. The transmission frequencies would need to be different to allow reception by the remote control system 302 of the independent signals, and of course, the remote control system will also need the discrimination capabilities to process each signal independently. For example, the output signal of the electrode 710 of ball 704 is received onto the central processing ball 714 where it is split to the input of two independent comparators, a comparator 716 and a comparator 718. Comparator 716 also receives the output of electrode 708 of ball 702, the resulting output of the comparator 716 being passed to a noise filter 720 to filter unwanted noise. The filtered analog signal is then converted to a digital signal using an A/D converter 722, and then transmitted from the monitor 700 at a first frequency $f_1$ of a transmission circuit 724 to the remote control station 302. Similarly, the other comparator 718 receives the output of electrode 712 of ball 706 and compares it to the output of electrode 710, the resulting output of the comparator 718 being passed to a noise filter 726 to filter unwanted noise. The filtered analog signal is then converted to a digital signal using an A/D converter 728, and then transmitted from the monitor 700 at a second frequency $f_2$ of a transmission circuit 730 to the remote control station 302. Within the CPU 312 of the remote control system 302, signals are mathematically processed using standard vector mathematics to determine vector magnitude allowing for an orientation-insensitive signal to be generated. This signal can be used to overcome any rotational bias created by the placement of the surface cardiac monitor 700 in a particular position on a patient.

Figure 8:
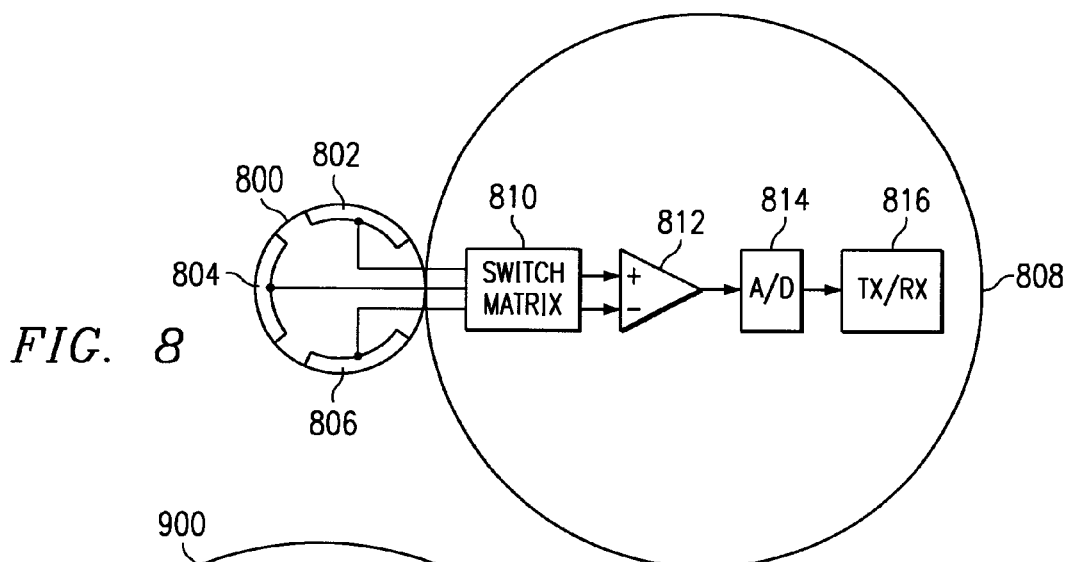
FIG. 8 illustrates an alternative 2-ball embodiment where a single ball semiconductor is fabricated with three electrodes oriented in three different directions.

Referring now to FIG. 8, there is illustrated an alternative 2-ball embodiment where a single ball semiconductor is fabricated with three electrodes oriented in three differing directions. An electrode ball 800 contains three electrodes 802, 804, and 806 oriented substantially orthogonally with one another. The electrode ball 800 connects to a processing ball 808 to facilitate signal processing of the signals from the three electrodes 802, 804, and 806. The outputs from each of the three electrodes 802, 804, and 806 are passed through interconnecting contacts (discussed in greater detail hereinbelow) to a switching matrix 810 on the processing ball 808. The switching matrix 810 operates to switch pairs of electrode outputs to the input of a comparator 812 (i.e., 802/804, 802/806, and 804/806). The comparator 812 output is then digitized using an A/D converter 814, and ultimately transmitted from the processor ball 808 using a transmit/receive circuit 816.

Figure 9:
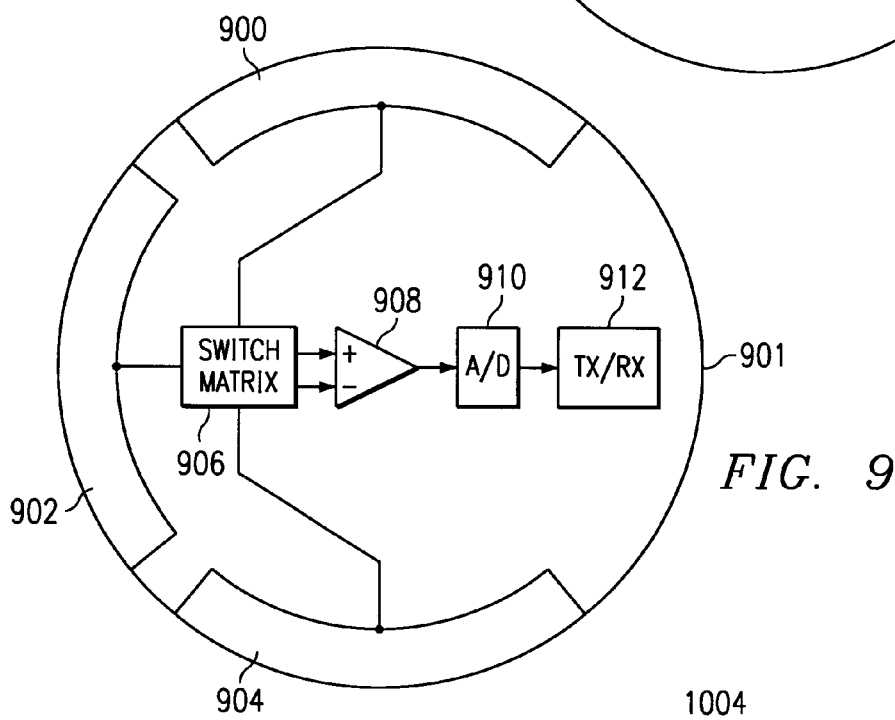
FIG. 9 illustrates a 1-ball alternative embodiment having three electrodes and the processing circuitry all positioned on one semiconductor ball.

Referring now to FIG. 9, there is illustrated a 1-ball alternative embodiment having three electrodes and the processing circuitry all positioned on one semiconductor ball 901. Three electrodes 900, 902, and 904 are fabricated substantially orthogonal to one another on a substrate of the ball 901 and whose outputs connect to a switch matrix 906 to switch any pair of electrode outputs to a comparator 908. The composite analog electrocardiogram output signal of the comparator 908 is then digitized using an A/D converter 910 and transmitted from the ball 901 to a remote control station 302 using a transmit/receive circuit 912. The signals from each electrode would be compared, processed, amplified, and digitalized all on one semiconductor ball in this embodiment. Software within the CPU 312 of the remote control station 302 will compare signals derived from each surface cardiac monitor to elicit any vectorial change in the electrocardiogram signal obtained from one surface cardiac monitor versus another surface cardiac monitor allowing the CPU 312 to detect dynamic changes in orientation and magnitude of electrical fields which occur under conditions of ischemic changes within cardiac muscle.

The distinct advantages of this surface cardiac monitor are the wireless nature of recording and transmission which frees the patient from wires and relay boxes. These wires and relay boxes may not be compatible with certain diagnostic imaging equipment. Current surface electrodes connected by wires to a relay box are constantly detached from the body, or disconnected from one another, because of the constant pull exerted by the wires attached to the box leading to malfunction.

Figure 10:
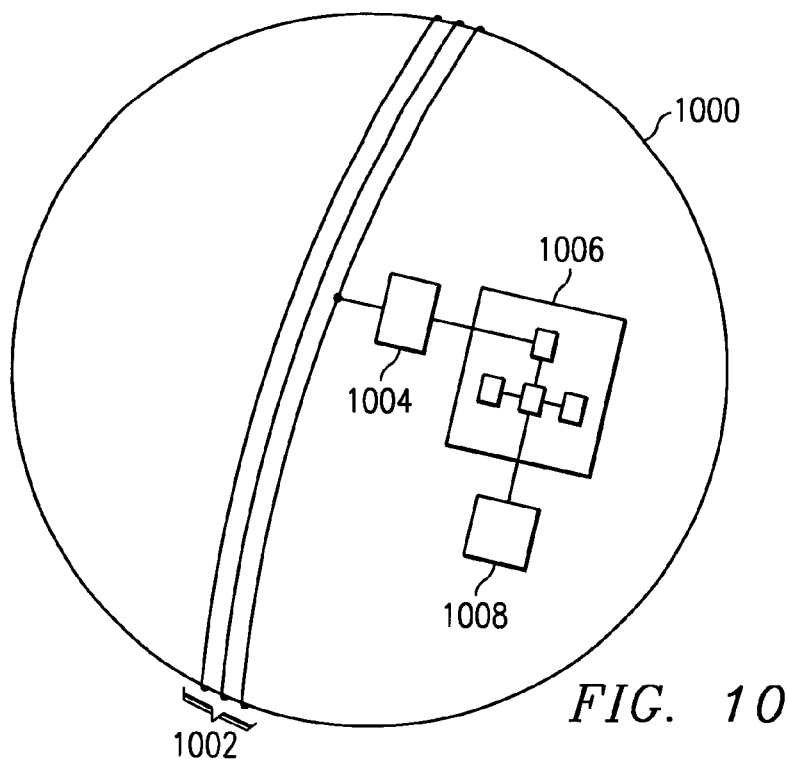
FIG. 10 illustrates a central processing ball having a single transmit/receive coil.

Referring now to FIG. 10, there is illustrated a central processing ball 1000 (similar to ball 208) having a single transmit/receive coil 1002. The antenna coil 1002 comprises several windings the number of which is determined according to the particular application. A greater number of windings increases the coupling of a received signal. The antenna coil 1002 connects to a power regulator circuit 1004 to provide stable power for any onboard circuitry. In this embodiment, the power regulator connects to receive/transmit circuitry 1106. In transmit mode, the output signal passes through the power regulator circuit 1004 to the antenna coil 1002. In receive mode, power and signal are coupled into the antenna coil 1002 where the power portion is stripped off by the regulator circuit 1004 to supply onboard power. The signal portion is passed through the regulator circuit 1004 to the transmit/receive circuit 1006 where it is demodulated from an RF carrier and passed to a processor section 1008. When the central processing ball 1000 receives electrode information from electrode balls (not shown), that electrode information is passed into the processor section 1008 for comparison, filtering, and digital conversion prior to being transmitted to the remote control station 302. Digitized data from processor section 1008 is applied to the RF transmit/receive section 1006 for modulation of the digitized data on an RF signal using, for example, Frequency-Shift Keying (FSK) techniques.

Figure 11:
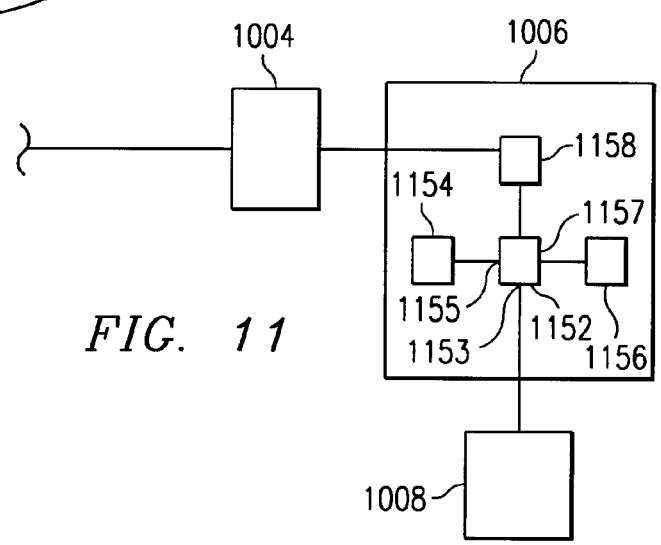
FIG. 11 illustrates a more detailed block diagram of the RF transmitter/receiver circuit of the central processing ball.

Referring now to FIG. 11, there is illustrated a more detailed block diagram of the RF transmitter/receiver circuit of the central processing ball 1000. The RF transmitter 1006 comprises a mixing circuit 1152, first and second RF oscillators 1154, 1156, and an amplifier 1158. In particular, the signal from an electrode corresponding to the level of current present during cardiac activity is digitized by the processor 1008 and applied to one input 1153 of mixing circuit 1152. A first high frequency signal from RF oscillator 1154 is applied to a second input 1155 of mixing circuit 1152, and a second low frequency signal from RF oscillator 1156 is applied to a third input 1157 of mixing circuit 1152. The mixing circuit 1152 modulates the incoming packet of digital information between a high frequency signal from RF oscillator 1154 for use in generating each logic "high" bit of data in the information packet; and a low frequency signal from RF oscillator 1156 for use in transmitting each logic "low" bit of data in the information packet. The resulting FSK signal is amplified by amplifier 1158 and applied to the coil 1002 for transmission to the RF receiver 310 (shown in FIG. 3) of the remotely located control station 302.

Fabrication of these kind of sensors can be readily adapted to a ball IC using the fabrication techniques described in commonly-assigned U.S. Pat. No. 5,955,776 entitled "Miniature Spherical-Shaped Semiconductor With Transducer," issued Sep. 21, 1999, and which is herein incorporated by reference. The performance of the monitor 200 can be protected from body tissues, or other of the body's defensive mechanisms by encapsulation of the device within a polymeric or gel coating albumin, or a "bio-coating." Examples of such encapsulation are described in the following U.S. Pat. No. 4,530,974 by Munro et al., entitled "Nonthrombogenic Articles Having Enhanced Albumin Affinity," issued Jul. 23, 1985; and 5,017,670 by Frautchi et al., entitled "Methods And Compositions For Providing Articles Having Improved Biocompatibility Characteristics," issued May 21, 1991, both of which are incorporated herein by reference.

Notably, the electrode sensor 210 is readily replaceable by other suitable sensors for sensing other physiological parameters such as pH, chemical parameters, and physical parameters such as pressure, movement, temperature and the like. For example, in applications where information regarding ionic activity or concentration is sought, one embodiment of a sensor utilizes an ion-sensitive field effect transistor ISFET which is essentially an insulated gate field effect transistor (IGFET) without its metal gate. The operation of the ISFET is similar to that of IGFET if one considers the reference electrode and the electrolyte into which the semiconductor ball is placed as the modified gate. In operation, the interfacial potential of the electrolyte-insulator interface produced by the net surface charge due to the ionization and complexation with the ions in a solution will affect the channel conductance of the ISFET in the same way as the external gate voltage applied to the reference electrode. The drain current of the ISFET is therefore a function of the electrolytes in solution for a constant drain-source voltage. Various materials can be used for the gate insulators, such as $SiO_2$, $Si_3N_4$ and $Al_2O_3$. For pH sensors, $Si_3N_4$ and $Al_2O_3$ provide satisfactory performance. ISFET's for other ions such as $K^+$, $Na^+$, and $Ca_2^+$ may have a layer coated over the gate insulator of valinomysin in PVC, aluminosilicate, and dedecyl phosphonate, respectively. Thus, the disclosed architecture is intended to be illustrative and not limited to only electrode applications.

Figure 12:
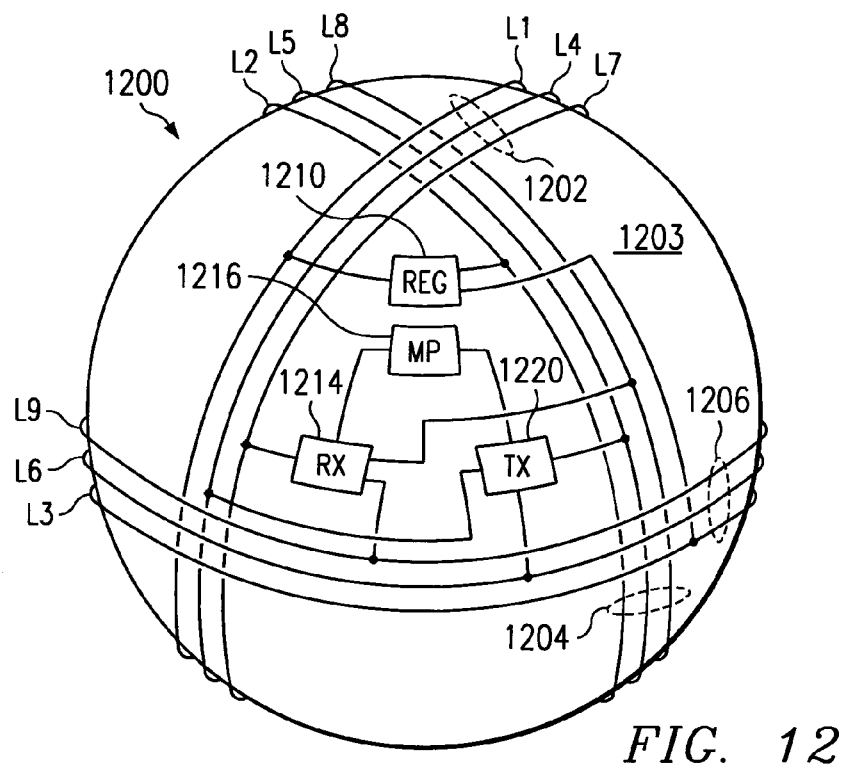
FIG. 12 illustrates an alternative embodiment of a central processor ball having three orthogonal coil structures.

Referring now to FIG. 12, there is illustrated an alternative embodiment of a central processor ball having three orthogonal coil structures. The processor ball 1200 (similar to processor ball 302) is fabricated on a substantially spherical substrate 1203, and includes nine coils $L_1$–$L_9$ in three sets 1202, 1204, and 1206 of three coils, each set 1202, 1204, and 1206 preferably orthogonal to each other so that power and signal communication requirements can be optimized according to the orientation of each processor ball 1200. Each coil set 1202, 1204, and 1206 comprises three coils; one transmit coil, one receive coil, and a power coupling coil. Therefore, in this embodiment, there are three power coils $L_1$, $L_2$, and $L_3$; three transmit coils $L_4$, $L_5$, and $L_6$; and three receive coils $L_7$, $L_8$, and $L_9$. The coils sets are grouped in this fashion to ensure that at least one coil set is orientated to provide potentially optimum power coupling and signal communication therewith. Onboard circuitry comprises a processor circuit 1216 for controlling all aspects of the processor ball 1200. The processor circuit 1216 can be a digital signal processor or other conventional processor. Power for the processor 1200 is provided via a regulator circuit 1210 which regulates power coupled into any of the power coils $L_1$, $L_2$, and $L_3$. Communications are provided by a transmit circuit 1220 and a receive circuit 1214. The transmit circuit 1220 connects to the three transmit coils $L_4$, $L_5$, and $L_6$ in order to provide transmit communications which are capable of outputting signals in any orientation of the processor 1200, and only one of which is included in one of the three sets of coils 1202, 1204, and 1206. Similarly, the receive circuit 1214 connects to each of the receive coils $L_7$, $L_8$, and $L_9$, in order to provide receive communications which are capable of receiving signals in any orientation of the processor ball 1200, and only one of which is included in each one of the three sets of coils 1202, 1204, and 1206. The coils $L_1$–$L_9$ can have any number of windings (not shown) in order to achieve the desired results.

The coils $L_1$–$L_9$ are connected by subsurface conductors (not shown) to the other circuit elements on the processor ball 1200. The processor 1216 provides an output to the transmitter 1220 that preferably radiates an RF signal to the external antenna 310 for processing by the CPU 312. The power regulator 1210 provides a relatively constant DC voltage of about 3.0 volts to the circuits on the processor ball 1200. A disclosed power source for the processor ball 1200 is provided externally by operation of the remote control system 302 utilizing the CPU 312 in conjunction with the antenna 310 which couples power to the power coils $L_1$, $L_2$, and $L_3$ in the form of a varying magnetic field. Alternatively, the processor ball 1200 can be powered by a miniature battery connected to the processor ball 1200 (which is discussed in greater detail hereinbelow). The miniature battery can also be in the shape of a ball (battery ball) configured to accommodate a common connection scheme for use between adjacent balls. Preferably, battery balls can be fashioned as electrical double-layer condensers from such materials as manganese dioxide, lithium or lithium ion, samarium-cobalt, carbon, etc. Since such a battery ball is a greater capacity energy source than an RF energy receiving coil, longer communication distances can be achieved by this means. Both the external magnetic field generator (CPU system 312) and receiver antenna 310 can be included in the same computer-controlled apparatus or remote CPU station 302 within proximity of the processor ball 1200, at least, but not limited to periods when its operation is required.

Figure 13:
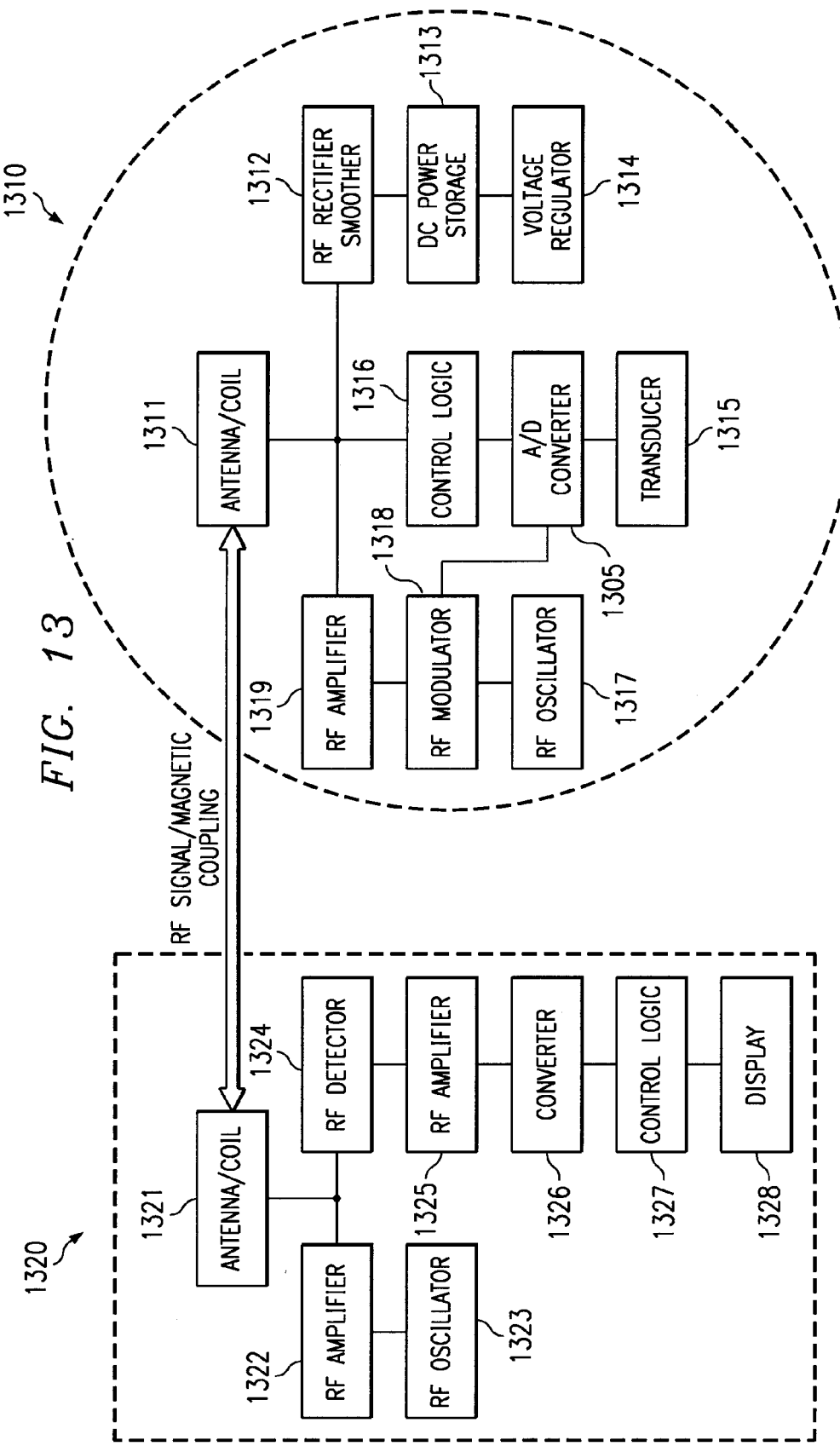
FIG. 13 illustrates a more detailed block diagram of an alternative embodiment having basic circuit functions of an external control system and a ball IC.

Referring now to FIG. 13, there is illustrated a more detailed block diagram of a disclosed monitor and control system. Processor ball 1310 (similar to processor balls 1200 and 208) includes an antenna/coil 1311, which serves the dual purpose of receiving signal energy from a remote control station 1320 (similar to control station 302) and transmitting signal energy thereto. The signal energy may be received by the antenna/coil 1311 by inductive coupling if the control station 1320 is sufficiently close to the processor ball 1310. Alternatively, electromagnetic waves can be used to transmit power from the control station 1320 to the processor ball 1310, whereby the magnetic field component of the electromagnetic wave induces a current in the coil 1311 in accordance with known techniques. The power signal received by the antenna/coil 1311 is rectified and smoothed by a RF rectifier/smoother block 1312. The output of the rectifier block 1312 is connected to a DC power storage block 1313, such as a capacitor. Such capacitor might also perform a waveform smoothing function. A voltage regulator 1314 is used to make the DC voltage stable regardless of the distance between the control station 1320 and the processor ball 1310.

The processor ball 1310 includes a transducer block 1315 which represents both the function of sensing quantitative conditions, and the function of an actuator, such as an impulse generator, having anode and cathode portions of an electrode, and flanking electrodes. Such semiconductor electrical sensors and impulse generators are known in the art, and can be adapted to fabrication on a spherical semiconductor substrate, as described hereinabove. An A/D converter 1305 is connected to the transducer 1315 to convert the electrical signal sensed by the transducer 1315 to a signal that can be transmitted out to the control station 1320. Notably, the converter 1305 can be part of the transducer 1315, such as a variable capacitor for generating a signal depending upon the variations in capacitance. Control logic 1316, which can be part of an onboard processor that controls not only the converter 1305 but also circuitry on the ball 1310, is provided in accordance with known techniques. An RF oscillator 1317 generates an RF signal at a predetermined frequency in the RF band. An RF modulator 1318 modulates the output of the converter 1315 onto the carrier frequency signal. The resulting modulated signal is amplified by an RF amplifier 1319, and then transmitted to the antenna/coil 1311. The technique for transmitting data from the ball 1310 to the main control station 1320 using the carrier frequency generated by the RF oscillator 1317 can be in the form using any suitable modulation and protocol. For example, the modulation can be AM, FM, PM, FSK or any other suitable modulation technique. Further details of the preferred coil are described in the aforementioned commonly-assigned U.S. patent application Ser. No. 09/448, 642 entitled "Miniature Spherical-Shaped Semiconductor With Transducer," and filed Nov. 24, 1999.

The external control station 1320 includes an antenna/coil 1321 that serves the dual purpose of generating the electromagnetic wave for transmitting power to the ball 1310, and receiving the RF data signal transmitted by the ball 1310. It is preferred that the frequency of the electromagnetic wave that is output by the antenna/coil 1321 is different from the carrier frequency generated by the RF oscillator 1317. An RF amplifier 1322 is used to couple the electromagnetic wave for power transmission to the antenna/coil 1321. An RF oscillator 1323 determines the frequency of the electromagnetic wave that is emitted by the control station 1320. The data received by the antenna/coil 1321 is detected by an RF detector 1324, and then amplified by an RF amplifier 1325. Preferably, the converter 1326 converts the signal from the RF amplifier 1325 to a digital signal, which in turn is input to a control logic block 1327. The control logic 1327 may be a smaller processor unit to interface with the main control station 1320. The control logic 1327 extracts the data from the signal received by the control station 1320 from the ball 1310, and displays that information on a suitable display 1328, such as a CRT screen.

Figure 14:
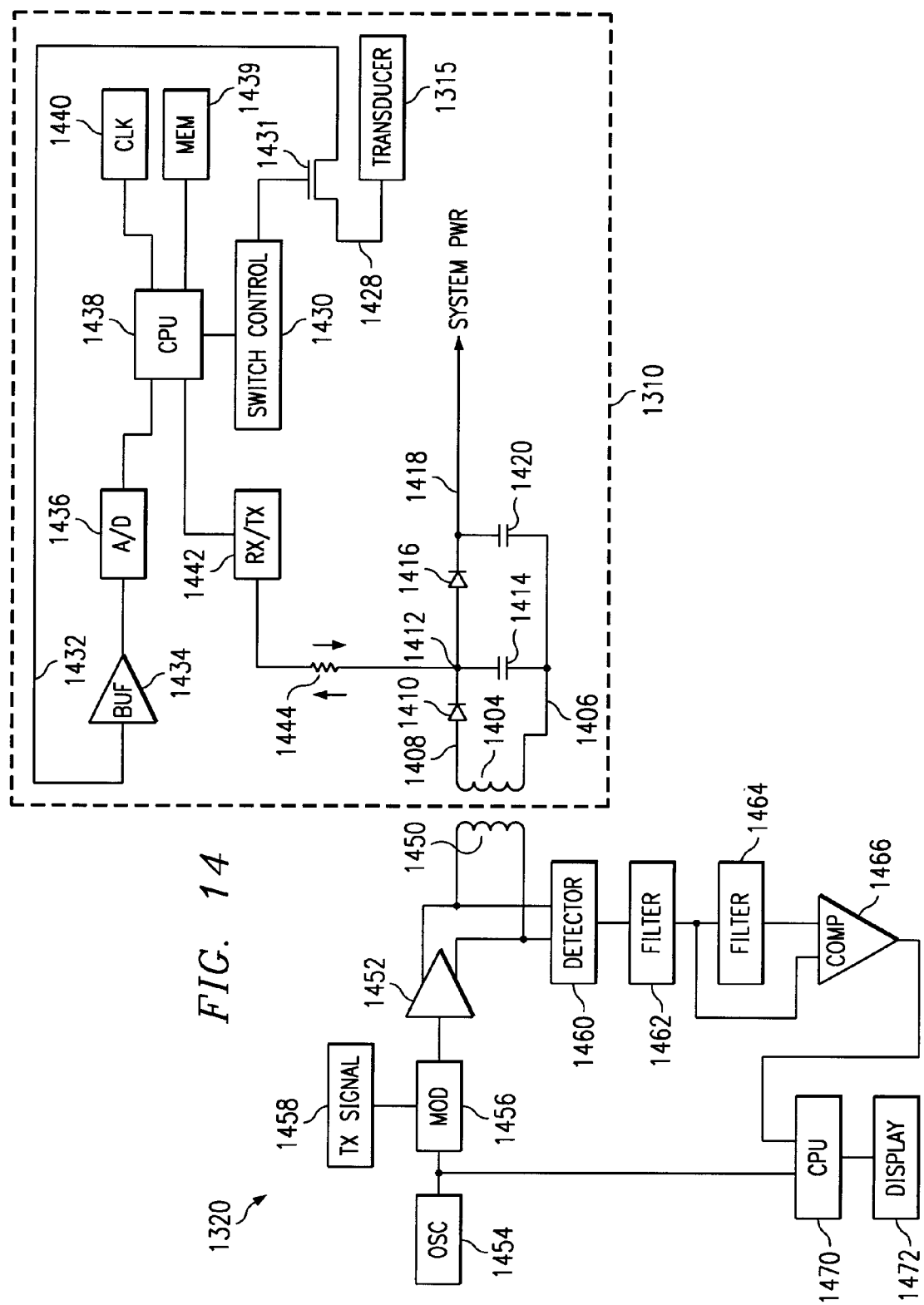
FIG. 14 illustrates a schematic block diagram of the control system and the ball IC for the powering/detection operation.

Referring now to FIG. 14, there is illustrated a schematic block diagram of the control system and the ball IC for the powering/detection operation. The ball IC 1310, as described hereinabove, is operable to provide the transducer 1315 for interfacing with the desired quantitative condition. The illustrated embodiment of FIG. 14 is that associated with a "passive" system, which term refers to a system having no battery associated therewith. In order to operate the system, there is provided an inductive coupling element 1404 in the form of an inductor, which is operable to pick up an alternating wave or impulse via inductive coupling, and extract the energy therein for storage in the inductive element 1404. This will create a voltage across the inductive element 1404 between a node 1406 and a node 1408. A diode 1410 is connected between the node 1408 and the node 1412, with the anode of diode 1410 connected to node 1408 and the cathode of diode 1410 connected to a node 1412. Typically, the diode 1410 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 1410 is operable to rectify the voltage across the inductive element 1404 onto the node 1412, which has a capacitor 1414 disposed between node 1412 and node 1406. Node 1412 is also connected through a diode 1416 having the anode thereof connected to node 1412 and the cathode thereof connected to a node 1418 to charge up a capacitor 1420 disposed between node 1418 and 1406. The capacitor 1420 is the power supply capacitor for providing power to the ball IC 1310. The capacitor 1414, as will be described hereinbelow, is operable to be discharged during operation of the system and, therefore, a separate capacitor, the capacitor 1420, is required for storing power to power the system of the ball IC 1310.

There is also provided a switching transistor 1431 which has one side of the gate/source path thereof connected to a node 1428 which is the output of the transducer 1315 and the other side thereof connected to a node 1432. The gate of transistor 1431 is connected to the output of the switch control 1430. Node 1432 is connected to the input of a buffer 1434 to generate an analog signal output thereof which is then converted with an A/D converter 1436 to a digital value for input to a CPU 1438. The CPU 1438 is operable to receive and process this digital input voltage. A clock circuit 1440 is provided for providing timing to the system. A memory 1439 is provided in communication with the CPU 1438 to allow the CPU 1438 to store data therein for later transmittal back to the remote location or for even storing received instructions. This memory 1439 can be volatile or it can be non-volatile, such as a ROM. For the volatile configuration, of course, this will lose all information when the power is removed. The CPU 1438 is operable to provide control signals to the switch control 1430 for turning on the transistor 1431 at the appropriate time. In addition to the transistor 1431 being toggled to read the transducer 1315, transistor 1431 could be a pass-through circuit such that the CPU 1438 can continually monitor the voltage at the output of the transducer 1315. System power to all power-consuming elements of the ball IC 1310 is provided at the SYSTEM PWR output node.

In order to communicate with the CPU 1438 for transferring data thereto and for allowing the CPU 1438 to transfer data therefrom, a receive/transmit circuit 1442 is provided for interfacing to node 1412 through a resistive element 1444. This allows RF energy to be transmitted to node 1412. It is important to note that the semiconductor junction across diode 1410 is a capacitive junction. Therefore, this will allow coupling from node 1412 to node 1408. Although not illustrated, this could actually be a tuned circuit, by selecting the value of the capacitance inherent in the design of the diode 1410. In any event, this allows an RF connection to be provided across diode 1410 while allowing sufficient energy to be input across conductive element 1404 to provide a voltage thereacross for rectification by the diode 1410 and capacitor 1414. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et. al., U.S. Pat. No. 3,944,982, entitled "Remote Control System For Electric Apparatus," issued Mar. 16, 1976, which are incorporated herein by reference. With these types of systems, power can continually be provided to the node 1412 and subsequently to capacitor 1420 to allow power to be constantly applied to the ball IC 1310.

The remote control system 1320 which is disposed outside of the body or away from the prosthesis and proximate to the ball IC 1310 includes an inductive element 1450 which is operable to be disposed in an area proximate to the skin, yet exterior to the body, in the proximity of the ball IC 1310, as close thereto as possible. The inductive element 1450 is driven by a driving circuit 1452 which provides a differential output that is driven by an oscillator 1454. This will be at a predetermined frequency and power level necessary to couple energy from inductive element 1450 to inductive element 1404. Since this is an external system, the power of the oscillator can be set to a level to account for any losses through the body tissues. To allow information to be transmitted, a modulation circuit 1456 is provided which is modulated by a transmitter signal in a block 1458 that allows information to be modulated onto the oscillator signal of the oscillator 1454, which oscillator signal is essentially a "carrier" signal. However, it should be understood that the information that is transmitted to the ball IC 1310 could merely be date information, whereas the CPU 1438 could operate independent of any transmitted information to provide the correct timing for the output pulses and the correct waveshape therefor. Alternatively, entire control of the system could be provided by the transmit signal 1458 and the information carried thereon, since power must be delivered to the illustrated embodiment due to the lack of any independent power in the ball IC 1310. In the present disclosure, the information transmitted to the ball 1310 is frequency selective or it is ID dependent. In the frequency selective mode, the transmit signal 1458 operates at a select frequency for a particular ball when multiple balls 1310 are imbedded. Each ball 1310 will be tuned to its associated frequency. This can be for both power and command information. In the ID mode, each ball 1310 has a particular ID associated therewith and stored in memory 1439, and will only create the stimulus when its ID is transmitted by the transmitter 1458. In this mode, all balls 1310 are powered at the same time. Additionally, the power levels can be reduced, such that a separate transmit circuit can be provided for each ball 1310 and disposed on the skin proximate to the associated ball 1310 with the central control system 1320 controlling the plurality of separate transmit circuits.

When the information is received from the ball IC 1310, it is superimposed upon the oscillator signal driving the inductive element 1450. This is extracted therefrom via a detector 1460 which has the output thereof input to a first low pass filter 1462, and then to a second low pass filter 1464. The output of low pass filters 1462 and 1464 are compared using a comparator 1466 to provide the data. The filter 1462 provides an average voltage output, whereas the filter 1464 provides the actual digital voltage output. The output of the comparator 1466 is then input to a CPU 1470 which also is powered by the oscillator 1454 to process the data received therefrom. This can then be input to a display 1472.

Figure 15A:
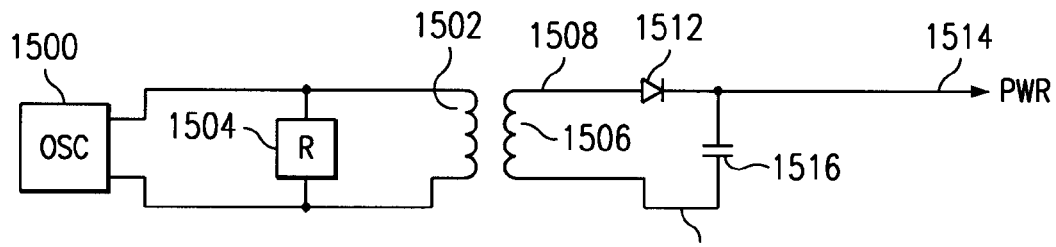
FIG. 15A illustrates an oscillator which drives an external inductive element.
Figure 15B:
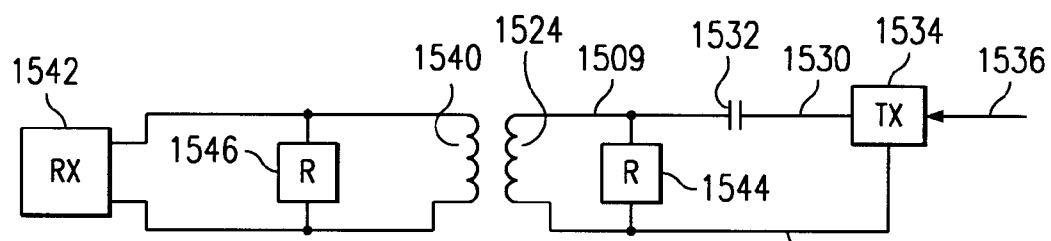
FIG. 15B illustrates the receive operation which utilizes a separate inductive element or antenna in the ball IC.
Figure 15C:
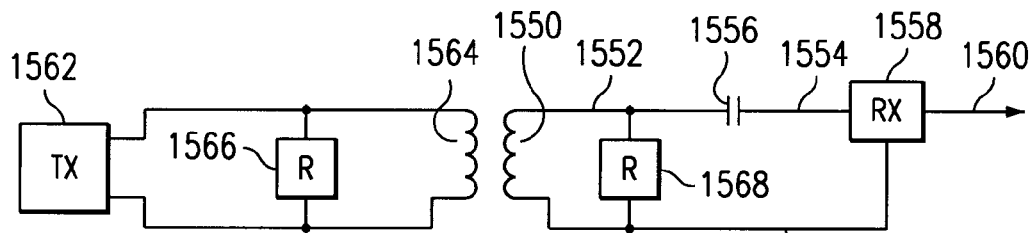
FIG. 15C illustrates a simplified schematic diagram of the receive portion.

Referring now to FIGS. 15A–15C, there are illustrated alternate embodiments for the transmit/receive operation. In FIG. 15A, there is provided an oscillator 1500 which drives an external inductive element 1502. Typically, there is some type of load 1504 disposed across the inductive element 1502. This is the primary power that is provided to the system. A separate inductive element 1506 is provided on the ball IC 1310, for being inductively coupled to the inductive element 1502. Thereafter, a voltage is generated across the inductive element 1506, the inductive element 1506 being connected between nodes 1508 and 1510. A diode 1512 is connected between node 1508 and a power node 1514, and a power supply capacitor 1516 is disposed across node 1514 and a node 1510. This allows the voltage on node 1508 to be rectified with diode 1512.

In FIG. 15B, the receive operation, in this alternative embodiment, utilizes a separate inductive element or antenna 1524 in the ball IC 1310, which is operable to be connected between nodes 1509 and 1511. Node 1509 is capacitively coupled to a transmit node 1530 with a capacitor 1532, the capacitor 1532 being a coupling capacitor. A transmitter 1534 is provided for transmitting received data from a line 1536 to the node 1530, which is then coupled to the node 1509 to impress the RF signal across the inductive element 1524.

A corresponding inductive element 1540 is disposed on the external remote controller of control system 1320, which inductive element 1540 is operable to be disposed proximate to the inductive element 1524, but external to the human body. The inductive element 1540 is basically a "pick-up" element which is operable to receive information and function as an antenna, and provide the received signal to a receiver 1542. The structure of FIG. 15B is a separate structure, such that node 1509 is isolated from node 1508, the power receiving node. However, it should be understood that any harmonics of the oscillator 1500 would, of course, leak over into the inductive element 1524. This can be tuned out with the use of some type of tuning element 1544 on the ball IC 1310 disposed across inductive element 1524, and also a tuning element 1546 disposed across the inductive element 1540, i.e., the antenna.

Referring now to FIG. 15C, there is illustrated a simplified schematic diagram of the receive portion. The ball IC 1310 has associated therewith a separate receive antenna or inductive element 1550 disposed between node 1513 and a node 1552. Node 1552 is capacitively coupled to a receive node 1554 with a coupling capacitor 1556. A receiver 1558 is provided for receiving the information transmitted thereto and providing on the output thereof data on a data line 1560. The receiver 1558 is operable to receive the RF signal, demodulate the data therefrom, and provide digital data on the output 1560. External to the human body and the ball IC 1310 is a transmitter 1562 which is operable to impress a signal across an external inductive element 1564. The inductive element 1564 basically provides the RF energy and is essentially tuned with a tuning element 1566. A corresponding tuning element 1568 is provided on the ball IC 1310 and disposed across inductive element 1550, the inductive element 1550 acting as an antenna, as well as the inductive element 1564.

Figure 16:
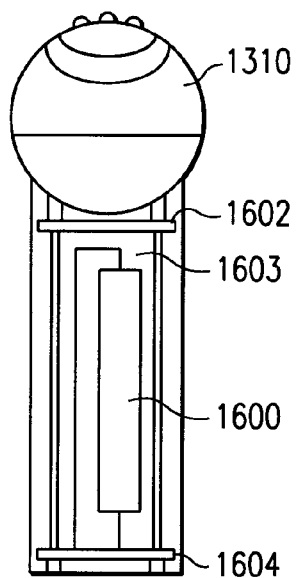
FIG. 16 illustrates a side view of an alternative embodiment utilizing additional circuitry or structure attached to the ball IC for providing a local power source.

Note that in circumstances where the signals of ball IC 1310 cannot be adequately received therefrom and/or power coupled thereto, the external location system 1320 may need to be inserted into the body proximate to the ball IC 1310 in order to couple the transmit/receive signals and power. Furthermore, where more than one ball 1310 is used, communication of power and data signals between the various ball ICs 1310 may need to employ distinct time periods (i.e., time multiplexing) when communication occurs using a single common frequency, or discrimination circuits may need to be used where communication occurs simultaneously with the plurality of implanted ball ICs 1310 having different oscillator frequencies. Referring now to FIG. 16, there is illustrated a side view of an alternative embodiment utilizing additional circuitry or structure attached to the ball IC 1310 for providing a local power source. As described hereinabove, the ball IC 1310 requires a power-generating structure for storing a power supply voltage such that diodes must be provided for receiving and rectifying a large amount of power and charging up a power supply capacitor. Alternatively, the ball IC 1310 could be configured to interface to an attached power supply system 1600 comprising either a battery or a capacitor. The local power supply system 1600 is illustrated as disposed on a circuit board 1603 defined by supporting structures 1602 and 1604. The circuit board 1603 contains electronics for interfacing the local power supply system 1600 to the ball IC 1310.

Figure 17:
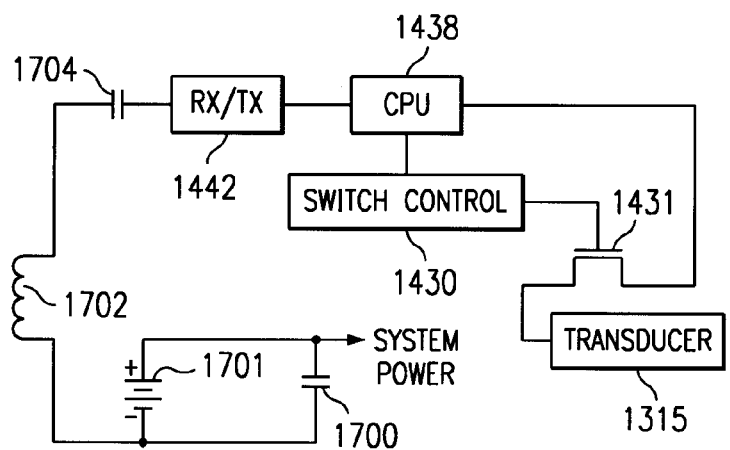
FIG. 17 illustrates a schematic block diagram of the ball IC using a battery as the local power supply system.

Referring now to FIG. 17, there is illustrated a schematic block diagram of the ball IC 1310 using a battery as the local power supply system 1600. A battery 1701 is provided as a source of self-contained power and is connected across a capacitor 1700 to provide smoothing of any power output to the system power-consuming elements of the ball IC 1310. Power for all onboard components is obtained from the SYSTEM POWER output by providing sufficient charge to the capacitor 1700. The capacitor 1700 could be formed on the surface of the ball IC 1310 or it could actually be part of the battery structure 1701. Additionally, the capacitance 1700 could actually be the capacitance of the battery 1701. Additional structure could be provided for powering the CPU 1438 and the other circuitry on the ball IC 1310 from the battery 1701. As such, there would only be required a smaller inductive element 1702 and a capacitor 1704 to allow the receive/transmit block 1442 to receive/transmit information from and to the remote exterior control station 1320. The switch control 1430 controls the gate of the switching transistor 1431 to switch output of the transducer 1315 through the switching transistor 1431 source/drain path to the CPU 1438.

Figure 18:
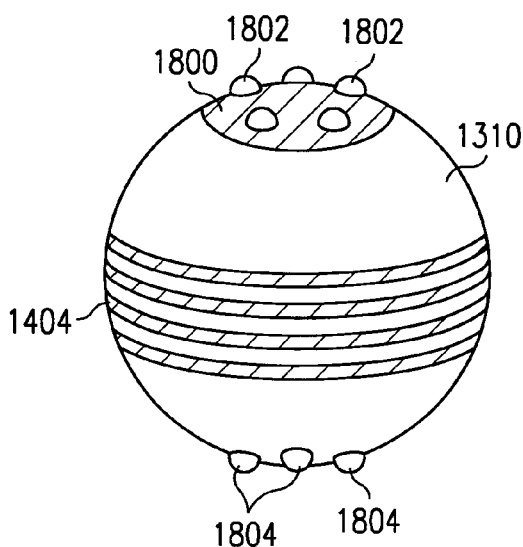
FIG. 18 illustrates a perspective view of the ball IC, wherein an inductive element is illustrated as being strips of conductive material wrapped around the exterior of the ball IC.

Referring now to FIG. 18, there is illustrated a perspective view of the ball IC 1310, wherein the inductive element 1404 (similar to inductive element 120) is illustrated as being strips of conductive material wrapped around the exterior of the ball IC 1310. The inductive element 1404 is formed of a conductive strip wrapped many times around the ball IC 1310. The length of inductive element 1404 depends upon the receive characteristics that are required. As described hereinabove with reference to FIGS. 15A–15C, there could be multiple conductive strips, one associated with a receive function, another for a transmit function, and another for a power function, or they could all share one single conductive element or strip. Notably, the inductive strips would be disposed on one side of the ball IC 1310 for communication purposes.

On one end of the ball IC 1310 there is provided a transducer interface 1800 of the transducer 1315 having, optionally, one or more interface balls 1802 (or partial balls, called nodules) associated therewith extending from the transducer interface surface to provide enhanced engagement of the measuring surface or physical entity. (Note that only a single sensor area is illustrated, although there could be more.) The interface balls 1802 can be made of nonreactive material, e.g., gold to prevent degradation while in the body. Note that in some applications, the interface nodules 1802 are not required for obtaining the desired quantitative data. On the other end of the ball IC 1310 are provided interconnect balls 1804 (or nodules) for interconnecting to one or more other spherical balls, as described hereinabove, which may provide similar functions such as monitoring of quantitative data, or unique functions such as supplying only power or data buffering and storage.

Figure 19:
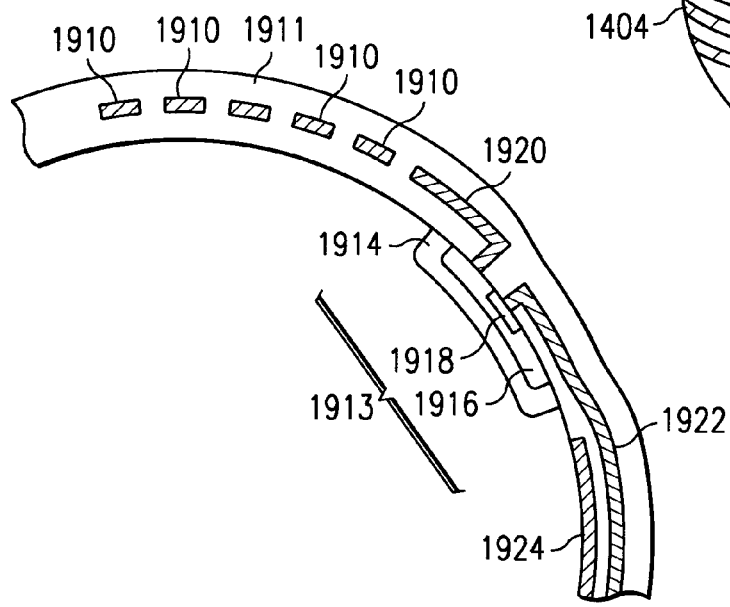
FIG. 19 illustrates a cross-sectional diagram of the surface of the ball IC illustrating the conductive strips forming the inductive element.

Referring now to FIG. 19, there is illustrated a cross-sectional diagram of the surface of the ball IC 1310 illustrating the conductive strips forming the inductive element 1404. The conductive strips are referred to by reference numeral 1910 which are spaced above the surface of the integrated circuit of the ball IC 1310 by a predetermined distance, and separated therefrom by a layer of silicon dioxide. A passivation layer 1911 is then disposed over the upper surface of the conductive strips 1910. The conductive strips 1910 can be fabricated from polycrystalline silicon but, it would be preferable to form them from the upper metal layer to result in a higher conductivity strip. This will allow the strips 1910 to be narrower and separated from each other by a larger distance. This separation would reduce the amount of capacitance therebetween.

One end of the strips 1910 is connected to a diode structure 1913. The diode structure 1913 is formed of an N-well implant region 1914 into which a P-well implant region 1916 is disposed, and an N-well implant region 1918 disposed within the P-well implant region 1916. This forms a PN diode where one end of the conductive strips 1910, a conductive connection 1920, is connected to the P-well 1916 implant region, and a conductive layer 1922 is connected at one end to the N-well implant region 1918. This conductive layer or strip 1922 extends outward to other circuitry on the integrated circuit and can actually form the capacitor. Since it needs to go to a capacitor directly, a lower plate 1924 formed of a layer of polycrystalline silicon or metal in a double-metal process, could be provided separated therefrom by a layer of oxide.

In another application, the sensor ball is used to stimulate excitable tissue. The semiconductor ball can function as a TENS (Transcutaneous Electrical Nerve Stimulator) unit. This is very important in treating chronic pain syndromes. The unit can also be used to stimulate both nerve and muscles in paralyzed or injured limbs to help prevent the development of atrophy or as a means to reduce the inflammatory response. Multiple balls which function as both receivers of electrical signal and also as transmitters of signal could function as a bridge between an amputated limb and a moveable prosthetic "hand."

Figure 20:
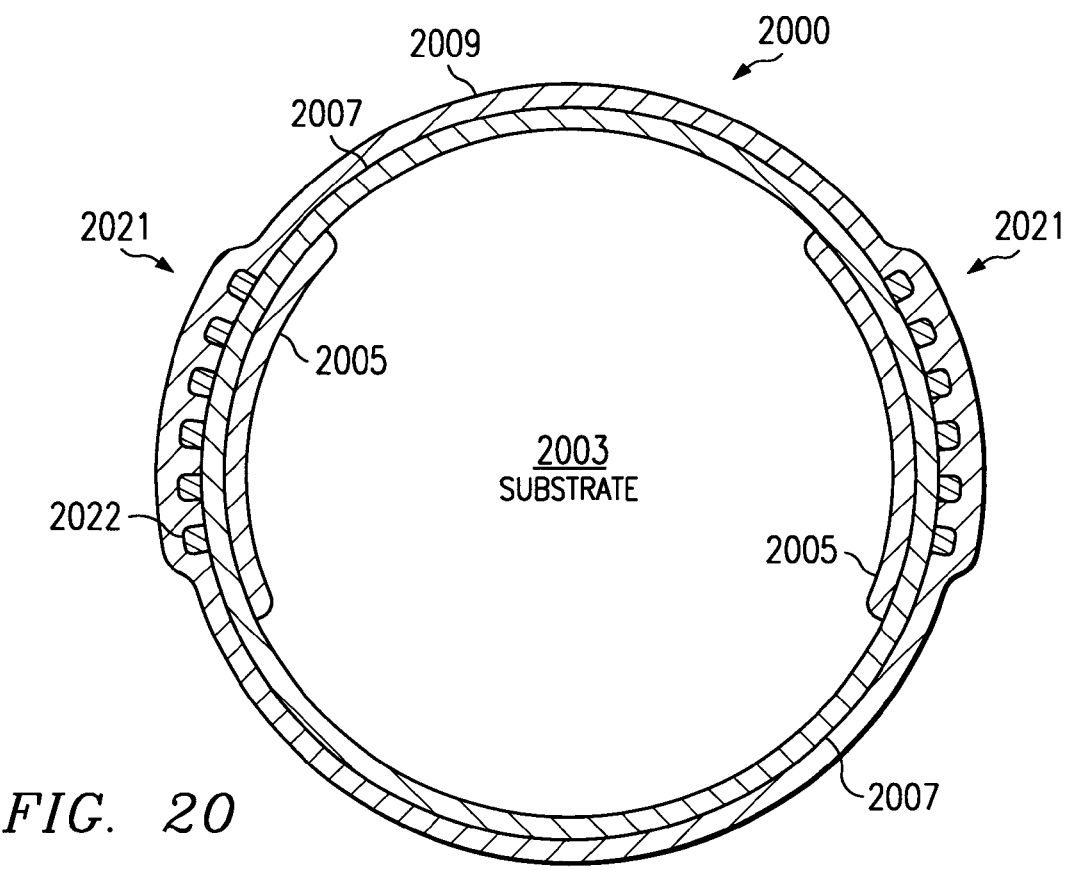
FIG. 20 illustrates a schematic block diagram of the ball IC in an actuator function and the remote control system for the powering/detection operation.

Referring now to FIG. 20, there is illustrated a cross section of a processor ball comprising a spherical-shaped semiconductor device on which an integrated circuit has been formed. Such a spherical-shaped integrated circuit semiconductor device is described in commonly assigned U.S. Pat. No. 5,955,776, issued Sep. 21,1999, and entitled "Spherical Shaped Semiconductor Integrated Circuit," the disclosure of which is referenced hereinabove. Processor ball 2000 (similar to processor balls 208, 1200, 1310, is built on the substantially spherical semiconductor substrate 2003, which may be doped P-type or N-type in accordance with the particular requirements of the fabrication process. Semiconductor circuitry indicated generally at 2005 resides on the substrate 2003. Circuitry 2005 includes the power regulator 1210, the transmit and receive circuits 1214 and 1220, the processor 1216, as well as other circuitry. The substrate 2003 and circuitry 2005 are covered with an insulating layer 2007 which is preferably formed of silicon dioxide or phosphosilicate glass. A power coil 2021 (one of $L_1$, $L_2$, and $L_3$), described with respect to FIG. 12, is formed of helically wrapped windings over the insulating shell 2007. The power coil 2021 may be fabricated from a deposited layer of aluminum (or copper, gold, etc.) that is patterned and etched using conventional semiconductor fabrication techniques. The actual number of individual windings 2022 of power coil 2021 may be more or less than the six shown in FIG. 20.

The processor ball 2000 is coated with or encapsulated in a coating layer 2009 of a biological inert material such as phosphosilicate glass. The coating 2009 is inert and can withstand potential chemical degradation into which it contacts, for example, the acidity of the stomach, to a very low pH level, and it is not subject to the enzymatic actions of the digestive tract. Processor ball 2000 is substantially spherical and preferably about one millimeter in diameter. The very small size of processor ball 2000 enables it to be embedded in surgical or medical tools and apparatus.

Referring now to FIG. 21, there are illustrated additional semiconductor details of a semiconductor processor ball. The processor ball 2000 is hermetically protected by a thin exterior glass passivation layer 2102, which may be phosphosilicate glass. The interior of the processor ball 2000 comprises a semiconductor substrate 2003, which may be doped p-type or n-type in accordance with the particular requirements of the fabrication process. Optionally, the substrate 2003 may be connected to, for example, a metallic intraluminal or a prosthetic device to serve as a ground potential for the processor ball 2000. In an embodiment where an electrode sensor 2104 is on the processor ball 2000, sensor 2104 has an outer surface 2106 that is exposed to the desired medium. The sensor 2104 preferably is formed atop a thick dielectric layer 2106, which may be a field oxide layer grown on the substrate 2003.

A large number of transistors T make up the circuitry of the voltage regulator 1210, processor 1216 and RF transmitter 1220, described above in connection with FIG. 12. Although these transistors T are depicted schematically as field-effect transistors, the integrated circuitry of the processor ball 2000 could also use bipolar transistors. The individual transistors T are shown separated by portions of the field oxide 2106. Transistor gates G and circuit interconnections (not shown) are embedded in an inter-level dielectric layer 2108 and are made using conventional semiconductor fabrication techniques adapted to the spherical surface of the processor ball 2000.

A power coil 2110 (as described in connection with antenna/coil 1002 of FIG. 10, or coils 1202, 1204, and 1206 of FIG. 12), is shown as having a plurality of separate windings 2112*a*, 2112*b*, 2112*c* and 2112*d*, which may be fabricated from a deposited layer of aluminum that is patterned and etched using conventional semiconductor fabrication techniques adapted to the spherical shape of the processor ball 2000. The windings 2112a, 2112b, 2112c and 2112d are insulated from each other by portions of the inter-level dielectric layer 2108. The actual number of individual windings of the coil may be far greater than the four specific windings 2112a, 2112b, 2112c and 2112d, shown. The ends of the coil 2110 are connected by additional conductors (not shown) to other circuit elements of the processor ball 2000.

Figure 22:
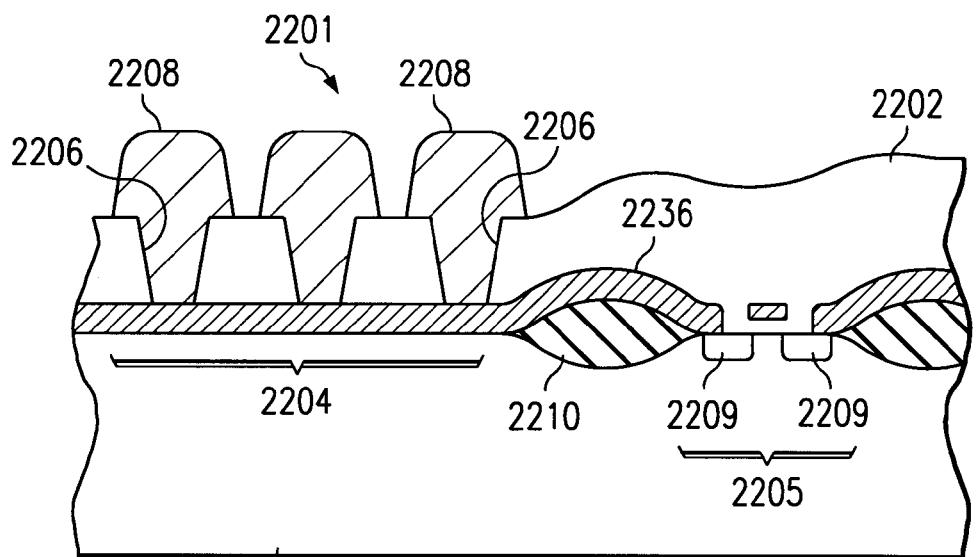
FIG. 22 illustrates a cross-sectional view of an electrode sensor pad.

Referring now to FIG. 22, there is illustrated a cross-sectional view of an electrode sensor pad 2201. In general, the pad 2201 is required to provide a conductive interface between the transistor 2205 and the desired medium. This therefore requires some type of metallic interface that is non-reactive. Such an interface would require a metal such as gold, platinum and the like. In the disclosed embodiment, gold would be provided. After the formation of the upper metal layer 2236 on a substrate 2200 via a deposition technique with metal such as aluminum or copper, a passivation layer of oxide 2202 is deposited to basically prevent oxidation of the metal layer 2236, and protect the semiconductor circuits, in general. The metal contact layer 2236 extends beyond the active region 2205 to a pad region 2204, and is separated from the active region 2205 by a layer of field oxide 2210 or some type of isolation oxide. There may be some type of channel stop implant disposed below the field oxide layer 2210. The metal contact layer 2236 extends from the source/drain implant 2209 to the region 2204. This metal contact layer 2236 is required to be fairly conductive. Typically, polycrystalline silicon is not of sufficient conductivity to meet this requirement. Therefore, some type of polysilicide process may be required, wherein the upper surface is converted to some type of silicide such as titanium disilicide to lower the surface resistivity thereof. Alternatively, a metal layer could be provided which is connected to the metal contact region 2236.

Once the contact region 2236 is formed, and the passivation layer 2202 is disposed over the entire structure, vias 2206 are formed therein. These vias 2206 are then filled with metallic plugs 2208 by forming a layer of metal over the oxide passivation layer 2202 and then etching the passivation layer 2202 to remove the undesired portions. The metal plugs 2208 may be formed of metal such as aluminum or gold. If they were formed of gold, this would allow for soldering if they were to be used as contacts. However, in this context, these plugs 2208 are utilized for conductivity purposes. Therefore, an aluminum plug would be sufficient if it were covered with a thin layer of gold to render the aluminum non-reactive and prevent oxidation thereof. Alternatively, in the disclosed embodiment, the plug may, of course, be gold. However, it should be understood that any type of non-reactive metal could be utilized as long as the surface thereof is sufficiently non-reactive and the conductance of the plug 2208 is sufficiently high to result in a low resistance path between the exterior of the spherical ball IC and a capacitive plate of the capacitor 2026. The reason for this is that the stored charge must be discharged into a resistance as low as 500 Ohms, and any significant resistance disposed between the upper plate of the capacitor 2026 and the exterior must be minimized.

Figure 23:
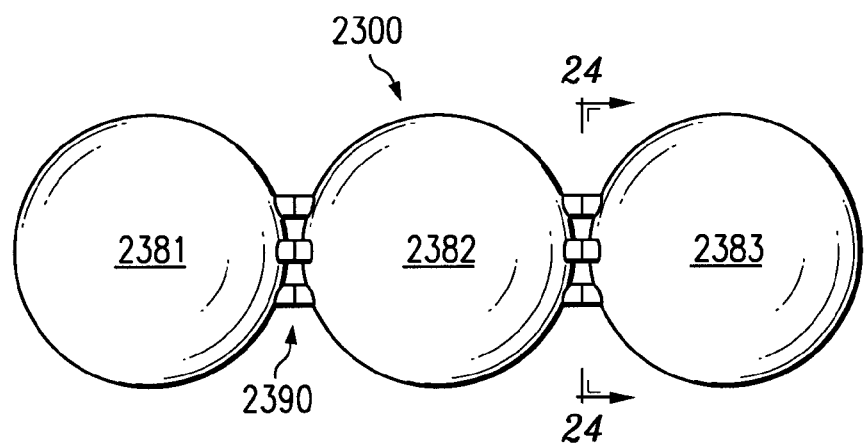
FIG. 23 illustrates a side elevation of a cluster of three semiconductor balls interconnected in a cooperative function.

Referring now to FIG. 23, there is illustrated a side elevation of a cluster 2300 of three semiconductor balls interconnected in a cooperative function. For example, ball 2381 (similar to ball 202) can include a single electrode for sensing heart electrical activity. Ball 2382 can include the processing functions of a processor ball (similar to ball 208), and ball 2383 can include a second electrode function. Connections between the balls are made through metal contacts 2390, which may be solder bumps, and as described in greater detail hereinbelow, the metal contacts 2390 may be used for a variety interface functions, such as power, data, and a signal bypass path.

Figure 24:
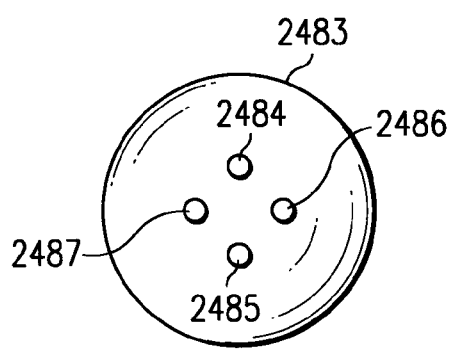
FIG. 24 illustrates a cross section of the ball interconnections taken through the line 24—24 of FIG. 23.

Referring now to FIG. 24, there is illustrated a cross section of the ball interconnections taken through the line 24—24 of FIG. 23. As mentioned hereinabove, the contacts 2390 may be employed to interface a variety of functions. For example, the contacts 2484 and 2486 may be power contacts, such as a positive 3.0 volts and ground, which can be passed from ball 2381 (if ball 2381 were to provide the power function for the set 2300) to ball 2382, and then around ball 2382 to ball 2383 by conductors on the surface of ball 2382 using two of a group of similar contacts of contacts 2390 to power ball 2383. The contacts 2485 and 2487 may be data and control contacts for communications between balls of the set 2300. Similar data and control contacts may exist among contact group 2390 between ball 2382 and ball 2383 to the extent needed.

Figure 25:
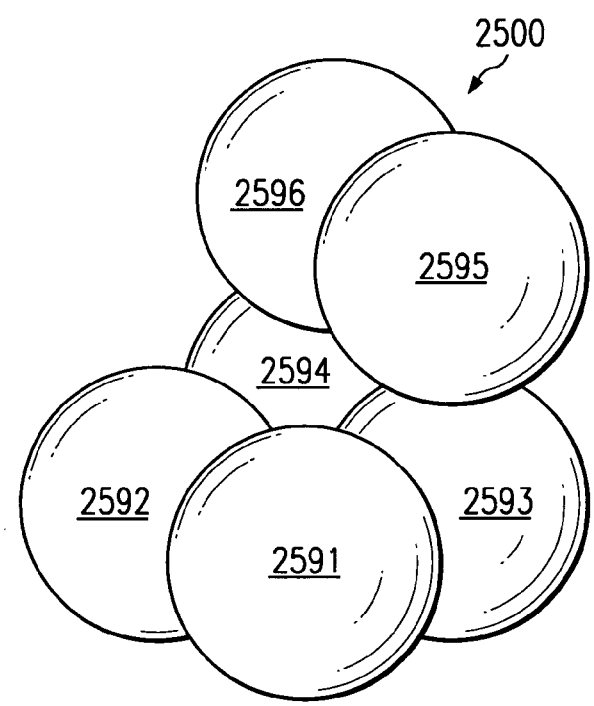
FIG. 25 illustrates a 3-D ball cluster in a cooperative orientation.

Referring now to FIG. 25, there is illustrated a 3-D ball cluster in a cooperative orientation. As an example of the versatility of such ball systems is illustrated where the cluster 2500 specifically shows six balls 2591, 2592, 2593, 2594, 2595 and 2596, arranged in a three-dimensional configuration. It will be appreciated that various other cluster arrangements are possible which have fewer balls, and are limited only by the constraints of the end-use application. Each of the balls 2591, 2592, 2593, 2594, 2595 and 2596, of the cluster 2500 can perform different electronic functions, and communicate with each other through contacts (not shown here, but discussed in detail in FIGS. 23 and 24). Such cluster arrangements can provide a mix of, for example, three battery balls 2591, 2592, and 2593, which provide ample power for the remaining energy-consuming balls, according to the functions provided. Such a mix may be necessary where a heating application is required for, for example, tumor ablation, or for more precise heating applications related to cartilage or ligament treatment.

Although the preferred embodiment has been described in detail, it should be understood that various changes, substitutions and alterations can be made therein without departing from the spirit and scope of the invention as defined by the appended claims.

What is claimed is:

1. A surface cardiac monitor system for monitoring electrical activity of the heart, comprising:
   one or more semiconductor electrode balls adaptable to be embedded in organic tissue, and/or dispersed adjacent thereto having respective electrode sensors for sensing electrical heart activity;
   a central processing semiconductor ball having each of said one or more semiconductor electrode balls connected electrically thereto for receiving respective heart signals from said sensors of said electrode balls, and processing said heart signals for transmission via a wireless communication link external to said organic tissue in which it is embedded; and
   a remote control system for receiving said transmitted heart signals and extracting heart information from said transmitted heart signal about the electrical activity of the heart.

2. The system of claim 1, wherein each of said one or more electrode balls is uniquely selectable by a respective unique frequency in a frequency mode, and by a unique ID stored therein in an ID mode, wherein in said frequency mode, one or more independent frequencies are transmitted to cause respective said one or more electrode balls to respond independently with said heart signals, and in said ID mode, one or more respective said unique IDs are transmitted to cause respective said one or more electrode balls to respond independently with said heart signals.

3. The system of claim 1, wherein said one or more semiconductor electrode balls are oriented substantially orthogonally from each other.

4. The system of claim 1, wherein said one or more semiconductor electrode balls and said central processing ball are substantially spherical.

5. The system of claim 1, wherein said one or more semiconductor electrode balls and said central processing ball are placed on the skin over the precordium anywhere from the sternum to the anterior axillary line in the $5^{th}$ intercostal space.

6. The system of claim 1, wherein said remote control system has a display for displaying said heart information.

7. The system of claim 1, wherein said one or more electrode balls is a single semiconductor electrode ball having three electrode sensors fabricated thereon in an orthogonal orientation, and said single electrode ball connects electrically to said central processing ball for processing of said heart signals.

8. The system of claim 1, wherein said electrode sensors are fabricated on the central processing ball such that the capabilities of sensing the heart activity and processing the heart in formation occurs on said central processing ball.

9. The system of claim 1, wherein said central processing ball comprises a comparator amplifier, a noise filter, and an analog-to-digital converter, said comparator amplifier receiving pairs of said electrode signals generated by pairs of said electrodes and generating an analog signal indicative of the comparison of said electrode signals; said noise filter removes noise signals from said generated analog signal; and said analog-to-digital signal converts said analog signal into a digital representative of the sensed electrical heart activity for transmission to said remote control system using said wireless communication.

10. The system of claim 9, wherein said central processing ball contains a matrix switch for switching pairs of said electrode signals into said comparator amplifier.

11. The system of claim 1, wherein said wireless communication for transmitting said heart signal is a telemetry transmitter device operating at radio frequency.

12. The system of claim 1, wherein said remote location receives said digitized transmitted heart signal is a telemetry receiver device operating at radio frequency.

13. The system of claim 1, wherein said central processing ball comprises first and second processing circuits which process electrode signals of said electrodes in a parallel, but non-linear fashion, by processing with said first processing circuit an electrode signal of a second electrode and an electrode signal of a first electrode, and by processing with said second processing circuit an electrode signal of said second electrode and an electrode signal of a third electrode.

14. A method of monitoring electrical activity of the heart with surface cardiac monitor system, comprising the steps of:

providing one or more semiconductor electrode balls having respective electrode sensors for sensing electrical heart activity;

disposing the one or more semiconductor balls proximate to the surface of the skin of an individual in such a manner as to selectively monitor electrical activity of the heart;

electrically connecting a central processing semiconductor ball to each of the one or more semiconductor electrode balls for receiving respective heart signals from the sensors of the electrode balls, and processing the heart signals for transmission via a wireless communication link; and receiving the transmitted heart signals at a remote control system heart information from the transmitted heart signal corresponding to the electrical activity of the heart.

15. The method of claim 14, wherein each of the one or more electrode balls in the step of providing are uniquely selectable by a respective unique frequency in a frequency mode, and by a unique ID stored therein in an ID mode, wherein in the frequency mode, one or more independent frequencies are transmitted to cause respective the one or more electrode balls to respond independently with the heart signals, and in the ID mode, one or more respective the unique IDs are transmitted to cause respective the one or more electrode balls to respond independently with the heart signals.

16. The method of claim 14, wherein the one or more semiconductor electrode balls in the step of providing are oriented substantially orthogonally from each other.

17. The method of claim 14, wherein the one or more semiconductor electrode balls and the central processing ball are substantially spherical.

18. The method of claim 14, wherein the one or more semiconductor electrode balls and the central processing ball are placed on the skin over the precordium anywhere from the sternum to the anterior axillary line in the $5^{th}$ intercostal space.

19. The method of claim 14, wherein the remote control system in the step of receiving has a display for displaying the heart information.

20. The method of claim 14, wherein the one or more electrode balls in the step of providing is a single semiconductor electrode ball having three electrode sensors fabricated thereon in an orthogonal orientation, and the single electrode ball connects electrically to the central processing ball for processing of the heart signals.

21. The method of claim 14, wherein the electrode sensors in the step of providing are fabricated on the central processing ball such that the capabilities of sensing the heart activity and processing the heart in formation occurs on the central processing ball.

22. The method of claim 14, wherein the central processing ball in the step of connecting comprises a comparator amplifier, a noise filter, and an analog-to-digital converter, the comparator amplifier receiving pairs of the electrode signals generated by pairs of the electrodes and generating an analog signal indicative of the comparison of the electrode signals; the noise filter removes noise signals from the generated analog signal; and the analog-to-digital signal converts the analog signal into a digital representative of the sensed electrical heart activity for transmission to the remote control system using the wireless communication.

23. The method of claim 22, wherein the central processing ball in the step of connecting contains a matrix switch for switching pairs of the electrode signals into the comparator amplifier.

24. The method of claim 14, wherein the wireless communication for transmitting the heart signal in the step of connecting is a telemetry transmitter device operating at radio frequency.

25. The method of claim 14, wherein the remote location in the step of receiving receives the digitized transmitted heart signal is a telemetry receiver device operating at radio frequency.

26. The method of claim 14, wherein the central processing ball in the step of connecting comprises first and second processing circuits which process electrode signals of the electrodes in a parallel, but non-linear fashion, by processing with the first processing circuit an electrode signal of a second electrode and an electrode signal of a first electrode, and by processing with the second processing circuit an electrode signal of the second electrode and an electrode signal of a third electrode.

27. A wireless EKG monitor, comprising:
one or more semiconductor electrode balls adaptable to be embedded on organic tissue, and/or dispersed adjacent thereto, having respective electrode sensors for sensing electrical heart activity; and
a central processing semiconductor ball having each of said one or more semiconductor electrode balls connected electrically thereto for receiving respective heart signals from said sensors of said electrode balls, and processing said heart signals for transmission via a wireless communication link external to said organic tissue in which it is embedded.

28. The system of claim 27, wherein said one or more semiconductor electrode balls are oriented substantially orthogonally from each other.

29. The system of claim 27, wherein said one or more semiconductor electrode balls and said central processing ball are substantially spherical.

30. The system of claim 27, wherein said one or more semiconductor electrode balls and said central processing ball are placed on the skin over the precordium anywhere from the sternum to the anterior axillary line in the $5^{th}$ intercostal space.

31. The system of claim 27, wherein said one or more electrode balls is a single semiconductor electrode ball having three electrode sensors fabricated thereon in an orthogonal orientation, and said single electrode ball connects electrically to said central processing ball for processing of said heart signals.

32. The system of claim 27, wherein said electrode sensors are fabricated on the central processing ball such that the capabilities of sensing the heart activity and processing the heart in formation occurs on said central processing ball.

33. The system of claim 27, wherein said central processing ball comprises a comparator amplifier, a noise filter, and an analog-to-digital converter, said comparator amplifier receiving pairs of said electrode signals generated by pairs of said electrodes and generating an analog signal indicative of the comparison of said electrode signals; said noise filter removes noise signals from said generated analog signal; and said analog-to-digital signal converts said analog signal into a digital representative of the sensed electrical heart activity for transmission to said remote control system using said wireless communication.

34. The system of claim 33, wherein said central processing ball contains a matrix switch for switching pairs of said electrode signals into said comparator amplifier.

35. A method of monitoring using a wireless EKG monitor, comprising:
providing one or more semiconductor electrode balls which are adaptable to be embedded in organic tissue, and/or dispersed adjacent thereto, having respective electrode sensors for sensing electrical heart activity; and
electrically connecting a central processing semiconductor ball having each of the one or more semiconductor electrode balls connected electrically thereto for receiving respective heart signals from the sensors of the electrode balls, and processing the heart signals for transmission via a wireless communication link external to the organic tissue in which it is embedded.

36. The method of claim 35, wherein the one or more semiconductor electrode balls in the step of providing are oriented substantially orthogonally from each other.

37. The method of claim 35, wherein the one or more semiconductor electrode balls and the central processing ball are substantially spherical.

38. The method of claim 35, wherein the one or more semiconductor electrode balls and the central processing ball are placed on the skin over the precordium anywhere from the sternum to the anterior axillary line in the $5^{th}$ intercostal space.

39. The method of claim 35, wherein the one or more electrode balls in the step of providing is a single semiconductor electrode ball having three electrode sensors fabricated thereon in an orthogonal orientation, and the single electrode ball connects electrically to the central processing ball for processing of the heart signals.

40. The method of claim 35, wherein the electrode sensors are fabricated on the central processing ball such that the capabilities of sensing the heart activity and processing the heart in formation occurs on the central processing ball.

41. The method of claim 35, wherein the central processing ball in the step of connecting comprises a comparator amplifier, a noise filter, and an analog-to-digital converter, the comparator amplifier receiving pairs of the electrode signals generated by pairs of the electrodes and generating an analog signal indicative of the comparison of the electrode signals; the noise filter removes noise signals from the generated analog signal; and the analog-to-digital signal converts the analog signal into a digital representative of the sensed electrical heart activity for transmission to the remote control system using the wireless communication.

42. The method of claim 41, wherein the central processing ball in the step of connecting contains a matrix switch for switching pairs of the electrode signals into the comparator amplifier.

* * * * *